United States Patent
Mei et al.

(10) Patent No.: US 11,307,206 B2
(45) Date of Patent: Apr. 19, 2022

(54) FUNCTIONALIZED METAL-LABELED BEADS FOR MASS CYTOMETRY

(71) Applicant: Deutsches Rheuma-Forschungszentrum Berlin, Berling (DE)

(72) Inventors: Henrik Mei, Berlin (DE); Axel Ronald Schulz, Berlin (DE); Lisa Budzinski, Berlin (DE)

(73) Assignee: DEUTSCHES RHEUMA-FORSCHUNGSZENTRUM BERLIN, Berlin (DE)

( * ) Notice: Subject to any disclaimer, the term of this patent is extended or adjusted under 35 U.S.C. 154(b) by 66 days.

(21) Appl. No.: 16/395,022

(22) Filed: Apr. 25, 2019

(65) Prior Publication Data
US 2019/0331689 A1    Oct. 31, 2019

(30) Foreign Application Priority Data

Apr. 27, 2018   (EP) .................................. 18169878

(51) Int. Cl.
```
G01N 33/58     (2006.01)
G01N 33/543    (2006.01)
G01N 33/566    (2006.01)
G01N 33/569    (2006.01)
```
(52) U.S. Cl.
CPC ..... *G01N 33/585* (2013.01); *G01N 33/54313* (2013.01); *G01N 33/566* (2013.01); *G01N 33/56972* (2013.01); *G01N 2458/15* (2013.01); *G01N 2560/00* (2013.01)

(58) Field of Classification Search
CPC .......... G01N 33/56972; G01N 33/566; G01N 33/585; G01N 33/54313; G01N 2560/00; G01N 2458/15
See application file for complete search history.

(56) References Cited

FOREIGN PATENT DOCUMENTS

| EP | 2 468 805 A1 | 6/2012 |
| JP | H08-48842 A | 2/1996 |
| WO | WO 2006/002472 A1 | 1/2006 |
| WO | WO 2006/083305 A2 | 8/2006 |

OTHER PUBLICATIONS

Chevier et al. Channel crosstalk correction in suspension and imaging mass cytometry. bioRxiv preprint doi: https://doi.org/10.1101/185744; this version posted Sep. 7, 2017, pp. 1-29 (Year: 2017).*
Abdelrahman et al. Lanthanide-containing polymer microspheres by multiple-stage dispersion polymerization for highly multiplexed bioassays. J. Am. Chem. Soc. 2009, vol. 131, pp. 15276-15283 (Year: 2009).*
Abdelrahman, A.I. et al. 2009 "Metal-containing polystyrene beads as standards for mass cytometry" J Anal Atomic Spectrometry 25: 260-268. *J Anal Atomic Spectrometry* 25: 15276-15283.
Abdelrahman, A.I. et al. 2010 "Metal-containing polystyrene beads as standards for mass cytometry" *J Anal Atomic Spectrometry* 25: 260-268.
Caterna, R. et al. 2016 "Enhanced Multiplexing in Mass Cytometry Using Osmium and Ruthenium Tetroxide Species" *Cytometry Part A* 89A: 491-4979.
European Search Report in corresponding European Application No. EP 18 16 9878.8, dated Oct. 25, 2018.
Szymanski, M.S. et al. 2013 "Preparation and quality control of silver nanoparticle-antibody conjugate for use in electrochemical immunoassays" *Journal of Immunological Methods* 387: 262-269.
Yang, J.W. et al. 2002 "Osmium Tetroxide Anchored to Porous Resins Bearing Residual Vinyl Groups: A Highly Active and Recyclable Solid for Asymmetric Dihydroxylation of Olefins" *Organic Letters* 4(26): 4685-4688.

* cited by examiner

*Primary Examiner* — Shafiqul Haq
(74) *Attorney, Agent, or Firm* — Knobbe, Martens, Olson & Bear, LLP

(57) ABSTRACT

Beads for use as a control, calibration and/or quantification probe in a mass cytometry assay, wherein the beads are labeled with a heavy metal selected from the group comprising osmium or ruthenium. Also disclosed are beads labeled with a heavy metal exhibiting a surface functionalization that allows for the binding of an affinity reagent, such as a metal-conjugated antibody. Methods are described for the labeling of the beads and usage of the beads for quantification of cell surface receptors or for a compensation of channel crosstalk in mass cytometry assays.

9 Claims, 26 Drawing Sheets

Fig. 7 a

| Bead | OsO₄ Staining | Capture Antibody Specificity | Functionality |
|---|---|---|---|
| BD™ CompBead (BD Biosciences) | (SI < 10³) | mouse | Validated as indicated in Tab. 2 |
| BD™ iCompBead (BD Biosciences) | (SI < 10³) | rat, hamster | Validated as indicated in Tab. 2 |
| Quantum™ SimplyCellular (Bangs Laboratories) | (SI < 10³) | mouse | Validated as indicated in Tab. 2 |
| AbC™ Total Antibody Beads (Thermo Fisher Inc.) | (SI < 10³) | mouse, hamster, rabbit, rat | Validated as indicated in Tab. 2 |
| OneComp eBeads (Thermo Fisher Inc.) | (SI < 10³) | mouse, rat, hamster | Validated as indicated in Tab. 2 |
| MACS® CompBead, anti-REA (Miltenyi Biotec) | (SI < 10³) | REA | Validated as indicated in Tab. 2 | a b

C c d

C

D Spiked-in osmium-labeled compensation beads

CD45+ live PBMC

FUNCTIONALIZED METAL-LABELED BEADS FOR MASS CYTOMETRY

The invention relates to beads for use as a control, calibration and/or quantification probe in a mass cytometry assay, wherein the beads are labeled with a heavy metal selected from the group comprising osmium or ruthenium. The invention further relates to beads labeled with a heavy metal exhibiting a surface functionalization that allows for the binding of an affinity reagent, such as a metal-conjugated antibody. Moreover, the invention relates to methods for the labeling of the beads and usage of the beads for quantification of cell surface receptors or for a compensation of channel crosstalk in mass cytometry assays.

BACKGROUND

Flow and mass cytometry are employed to characterize cellular systems at singe-cell resolution. Flow cytometry involves the analysis of optical signals produced by biological cells or suspensions of particles passing in a fluid stream through a focused beam of light. By means of a fluorescent label specific to cell components, such cell receptors on the surface, the amount of labeled components can be detected when the particle or cell traverses the beam of light. Flow cytometry is routinely used in basic research, to interrogate populations of biological cells that may show cell type or gene/protein expression heterogeneity, in the diagnosis of medical conditions and other applications in research and clinical practice. Deficiencies of flow cytometry are related to limitations in regard to staining techniques and spectral overlap of fluorochromes, which may lead to an incorrect assignment of the signal. Fluorescent based flow cell cytometry is therefore typically limited to the measurement of only a few fluorochromes simultaneously.

A recent technique aimed to overcome these limitations is mass cytometry, which at its core combines flow cytometry with mass spectroscopy (Bandura et al. Anal. Chem. 81, 2009). In analogy to flow cell cytometry, coupling probes are aimed to specifically target an antigen on a cell or a particle. In contrast to flow cell cytometry the label of the coupling probes is not a fluorophore, but a stable heavy metal isotope. Due to the unique atomic weight signature the heavy metal isotope can be distinguished in a mass cytometer with high accuracy and little overlap. As a unique feature, mass cytometry allows the use of over 40 coupling probes and the assessment of as many parameters at a single cell level (H. Spitzer et al. *Cell*, 165 2016, O. Ornatsky et al. *J Immunol Methods*, 361 2010).

In a typical mass cytometry assay, the cells of interest are incubated with metal-conjugated antibodies that serve as affinity reagents. During the incubation, the metal-conjugated antibodies bind to the cellular targets of interest and constitute a quantitative reporter for the presence of said targets. Subsequently, the cells are passed to a single cell suspension nebulizer and guided towards an inductively coupled plasma mass spectrometry device (ICP-MS). By passing an argon plasma, molecular bonds are broken and the metal-reporters are ionized. The resulting cloud of ions is typically sent through a quadrupole to enrich the signal of the metal reporter ions by a separation of mass-to-charge ratio in a time-of-flight mass cytometer. The transmitted ions are focused under the same acceleration potential such that the time-of-flight (TOF) of the mass ions to the detector exhibit a square-root dependence on the ion mass.

Mass cytometry assays have also been adapted to high dimensional imaging using laser ablation of tissue sections (Giesen et al. *Nat. Methods* 11, 417-422, 2014)) or in multiplexed ion beam imaging (MIBI) (Angelo et al. *Nat. Methods* 20, 436-442, 2014).

While the use of metal isotopes in mass cytometry reduces crosstalk among measurement channels, isotopic impurity, oxide formation, and instrument properties may still lead to signal spill-over, demonstrating the need for compensation or calibration methods (Chevrier et al., Cell Systems 6, 2018).

In fluorescence based flow cell cytometry, small nanoscale- or microscale sized particles (beads) emitting fluorescent light are routinely used to assist in instrument setup, data curation, or for achieving additional information from the acquired cell samples.

These include assays generating compensation controls, in which antibody capture beads are loaded with a particular antibody used in a cytometric assay, and which serve as a reference for calculating the extent of fluorescent spillover between cytometric channels for subsequent correction of raw data (Perfetto et al. *Nat. Protoc.* 1, 2006). For the quantification of cellular receptors, fluorescent signals elicited by sets of beads that are equipped with known, gradually increasing amounts of antibody capturing sites and which have captured the fluorescence-tagged antibody detecting the receptor of interest, serve as a reference for approximating the absolute number of receptors expressed on the surface of a given cell (Lenkei, R., B. Andersson. *J Immunol Meth*, 183(2), 1995). In additional assays, beads serve as a spike-in reference for normalizing cell counts (such as in the BD TruCount assay, Mandy F, Brando B. Curr Protoc Cytom. 2001 May; Chapter 6), as a solid phase for multiplexed enyzme-linked immunosorbent assays (ELISA) as implemented in the Luminex platform or the cytometric bead assay (CBA) (Elshal M F, McCoy J P. *Methods* (San Diego, Calif.). 2006), or for phagocytosis assays (Gu, et al. *Cytometry*, 85, 2014).

In flow cytometry, the beads are routinely detected based on their distinctive light scatter properties (primary signal). The signal of interest, commonly fluorescence (secondary signal) is then detected in a distinct detection channel. Mass cytometry has no analogue to light scatter, impeding a straight forward adaptation of these assays.

Some bead-based assays have been introduced in mass cytometry e.g. for quality control of antibody conjugates and compensation (Baumgart et al. *Cytometry* A. 91, 2017; Mei et al. *Cytometry* A. 89, 2016; Chevrier et al., *Cell Systems* 6, 2018). In these assays the detection of beads mainly relies however on the secondary signal associated with the beads (often that of the captured antibody conjugate), which is meant to be quantified and therefore cannot serve as a reliable independent control. In the example of antibody capture beads, insufficient antibody capturing, or low metal labeling of the captured antibody can result in that only a non-random fraction of beads is detected by the combined instrument and algorithm setup, and a variable fraction of beads remains undetected. As a result, bead-based data can be compromised in cases where the secondary signal is low, absent or variable. For instance, if the control bead were not successfully loaded with an antibody, there is no possibility to independently confirm the presence of beads in the injected sample.

Lanthanide-containing polystyrene beads have also been proposed as standards for a mass cytometer (Ahmed I. Abdelrahman et al. *Anal At Spectrum.* 2010; 25(3): 260-268). However, the application of these beads is limited to the calibration of a mass cytometer instrument.

In light of the prior art, there remains a significant need to provide additional means for control, calibration or compensation in mass cytometry assays and to allow for reliable quantification assay.

SUMMARY

In light of the prior art the technical problem underlying the present invention is to provide alternative and/or improved means for conducting mass cytometry assays that ensure a reliable read-out and quantitative measurements.

The problem is solved by the features of the independent claims. Preferred embodiments of the present invention are provided by the dependent claims.

In one aspect the invention therefore relates to beads for use in a mass cytometry assay, wherein the beads are labeled with a heavy metal preferably selected from the group comprising osmium or ruthenium.

In a further aspect the invention relates to a method of analyzing beads as control, calibration and/or quantification probes in a mass cytometry assay, comprising the steps of
 a. providing a mass cytometer
 b. providing cells to be probed in said mass cytometer
 c. providing beads, the beads are labeled with a heavy metal selected from the group consisting of osmium and ruthenium
 d. performing a mass cytometry assay including the steps of incubating the cells with one or more mass tagged affinity reagents and conducting an elemental analysis of said cells and beads using the mass cytometer,
wherein said beads are analyzed as a control, calibration and/or quantification probe in said mass cytometry assay.

The "labelling of the bead with the heavy metal" as used herein refers to an attachment or coupling of the heavy metal to the bead. Preferably, labelling refers to the attachment or coupling of a heavy metal to a synthetic polymer bead, preferably comprising polystyrene, that results from a reaction of a heavy metal tetroxide with a synthetic polymer, preferably polystyrene. In some embodiments, the labelling may thus refer to a covalent coupling, preferably resulting from a reaction of a tetroxide with a polystyrene. While covalent couplings are preferred in some embodiments, non-permanent attachments may also be envisioned. In some embodiments, the labelling is characterized by a stable association of the heavy metal with the bead after storage of at least 1 week at 4° C. The stable association may be for instance tested by determining the detection signal of two control groups of heavy metal labeled beads at different time points. At time point zero the heavy metal is detected in a first control group of labeled beads directly after the labelling, while a second control group is stored at 4° C. for one week and subsequently tested. Stable association refers to a decline of the detection signal, for instance in a mass cytometry assay, of less than 50%, preferably less than 30%.

It is preferred that the labelling of the bead with a heavy metal refers to a direct attachment or coupling of the heavy metal to the material that the bead is made of, e.g. a synthetic polymer such as polystyrene. The labelling of the bead with a heavy metal is therefore distinct from an indirect labelling of a bead with a heavy metal via for instance a heavy metal-conjugated antibody that binds to a surface functionalized bead.

The term "bead" as used herein means any solid particle that is suitable for mass cytometry assays described herein. In preferred embodiments, the bead has a size of about 1 nm to 200 µm, preferably 10 nm to 100 µm, preferably 100 nm to 100 µm, preferably 1 µm to 100 µm, preferably 1 µm to 50 µm, preferably 1 µm to 15 µm. Sizes or ranges defining size formed between any two values of the following are preferred: 0.5 µm, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0, 14.1, 14.2, 14.3, 14.4, 14.5, 14.6, 14.7, 14.8, 14.9, 15.0 µm. The size of the beads refers to their largest dimension along any axis crossing the geometric center. For spherical bead the size of the bead is thus the diameter.

The beads can be made of a variety of different materials including polystyrene, polyacrylic acid, polymethacrylic acid, polyacrylamide, polyglycidyl methacrylate, polypropylene, polyvinyl chloride, polyethylene, polychlorotrifluoroethylene carbonate, silicone resin or synthetic polymer compounds such as silicone rubber, porous glass, ground glass, latex or alumina. Preferred materials are synthetic polymers, in preferred embodiments synthetic polymers capable of labelling by a heavy metal oxide, more preferably capable of labeling by a heavy metal a tetroxide.

The beads are generally not limited to a certain shape, they are preferably essentially spherical, or preferably are uniform spheres, but other shapes are possible, such as cubes, prisms, pyramids, cylinders, cones, or other tetrahedrons of varying face number.

The aforementioned dimensions and properties of the beads allow the use of the bead as a control, calibration and/or quantification probe in mass cytometry assays. Mass cytometry may refer to an assay, that combines elemental mass spectrometry with flow cytometry in order to analyze cells using binding reagents that are "mass tagged", i.e., tagged with an element or isotope having a defined mass, preferably a heavy metal element or isotope. The mass tag corresponds to the fluorescent tag of conventional flow cell cytometry assay. In a typical mass cytometry assay the cells to be probed are introduced into a mass cytometer, where they are individually atomized and ionized. The individual cells are then subjected to elemental mass spectroscopy, which identifies and measures the abundance of the mass tags used.

As described herein the use of the bead as a control, calibration and/or quantification probe in a mass cytometry assay refers to an assay in which the beads are guided into a mass cytometer in addition to the cells of interest such that an independent signal stemming from said beads can detected.

As used herein a "mass cytometry assay" thus refers to a method for analyzing individual cells or particles by subjecting them to an elemental analysis using mass spectroscopy.

The general principles of mass cytometry, including methods by which single cell suspensions can be made, methods by which cells can be labeled using, e.g., metal-tagged antibodies, methods for atomizing particles and methods for performing elemental analysis on particles, as well as hardware that can be employed in mass cytometry, including flow cells, ionization chambers, reagents, mass spectrometers and computer control systems are known and are reviewed in a variety of publications including, but not limited to Bandura et al Analytical Chemistry 2009 81

6813-6822, Tanner et al (Pure Appl. Chem 2008 80: 2627-2641), U.S. Pat. Nos. 7,479,630, 7,135,296 and U.S. patent application 2008/0046194, for example, which publications are incorporated by reference herein for disclosure of those methods and hardware.

In brief, in preferred embodiments, a mass cytometry assay will include the provision of a mass cytometer comprising an introduction system for introducing particles (such as the cells or beads) sequentially into a device to substantially vaporize, atomize and excite or ionize the particles. To this end typically a nebulizer may be used that produces an aerosol comprising a single stream of particles. Furthermore, the mass cytometer comprises the device to vaporize, atomize and excite or ionize the particles and a mass spectrometer to individually analyze elemental composition of the vaporized, atomized and excited or ionized particles. In order to vaporize, atomize and excite or ionize the particles and analyze their elemental composition preferably inductively coupled plasma mass spectrometry (ICP-MS) can be used, which couples an inductively coupled plasma ionization source to a mass spectrometer. Herein, commonly an aerosol produced by nebulization is injected into a high temperature atmospheric pressure plasma obtained by the coupling of radio frequency energy into the flowing argon gas stream. The resultant argon plasma leads to a prompt vaporization, atomization and ionization of the particles. The resultant plasma containing the ionized components is extracted into vacuum, where the ions are separated from neutral species and subjected to a mass analysis using a time-of-flight measurement.

In a typical mass cytometry assay the cells of interest will be incubated with affinity reagents that are mass tagged with a heavy metal. Since the mass tagged affinity reagents are chosen to specifically bind cellular target molecules, the quantity of mass tagged affinity reagents allows for a determination of the presence of the cellular target molecules. Most commonly metal-conjugated antibodies may be used as mass tagged affinity reagents.

While preferably mass cytometry assay thus refers to the combination of flow cell cytometry and mass spectroscopy as described above, as used herein a mass cytometry assay may more generally refer to assays that adapted the principles of mass cytometry to further assays such as high dimensional imaging using laser ablation of tissue sections (see e.g Giesen *Nat. Methods* 11, 417-422) or multiplexed ion beam imaging (MIBI) (see e.g. Angelo et al. *Nat. Methods* 20, 436-442). In these assays, cells tagged with metal-conjugated antibodies are not introduced as an individualized fluid stream in a mass spectrometer, but entire tissue can be stained and subsequently analyzed using elemental analysis of a mass spectrometer. In these types of mass cytometry assays the properties of individual cells or particles can be assessed as a localized signal in the acquired mass cytometer images.

In some embodiments the step of conducting an elemental analysis of cells and beads using the mass cytometer in the method described herein encompasses an introduction of said cells and beads into a mass cytometer, preferably as individualized fluid stream, and subjecting them to an elemental analysis, preferably by vaporizing, atomizing and excite or ionize the cells and performing time-of-flight measurements. The introduction of said beads and cells may be r simultaneously or sequentially.

In some embodiments the step of conducting an elemental analysis of cells and beads using the mass cytometer in the method described herein encompasses a high dimensional imaging using laser ablation of tissue sections (see e.g Giesen *Nat. Methods* 11, 417-422) or multiplexed ion beam imaging (MIBI) (see e.g. Angelo et al. *Nat. Methods* 20, 436-442).

In some embodiment the beads as described herein may also preferably be used for biochemical assays for conventional elemental analysis in an ICP-MS. For instance the labelled beads may be tagged with a specific antibody and used to enrich for rare target molecules, e.g. to determine an association with or without heavy metals that without the labelled beads is difficult in complex mixtures of cell lysates.

The inventors have realized that mass cytometry assays as described in the prior art may profit from reliable control, calibration or compensation means and methods. The beads labeled with a heavy metal selected from the group comprising osmium or ruthenium provide excellent means.

Contrary to previous control or compensation beads that relied on metal-conjugated antibodies the beads according to the invention may be reliably detected due to the heavy metal signal of osmium or ruthenium. In this regard osmium or ruthenium have proven to be particularly suited, since they do not interfere with the atomic weight signature of common primary metal-conjugated antibodies for use in mass cytometry assays. Commonly used metal-conjugated antibodies are often based on elements or isotopes that lead to detection signal in a mass spectrometer between 140 and 175 molecular weight (MW), such as e.g. Lanthanum (MW 135-141), Neodymium (MW 142-150) or Gadolinium (MW 148-160). Advantageously, the detection signal of osmium with a typical molecular weight signature in between 184-190 or ruthenium with a typical molecular weight signature in between 94 and 104 can be distinguished from common, commercially available metal-conjugated antibodies. Osmium and ruthenium may therefore serve as excellent independent control tags allowing a bead detection that does not interfere with the detection of target specific metal-conjugated antibodies.

Furthermore, experiments have shown that labelling of the beads with osmium and ruthenium advantageously and surprisingly does not interfere with a surface functionalization of the beads. Therefore, beads labeled with osmium and ruthenium may in addition have intact functionalized surface groups e.g. antibody capturing sites for an attachment of metal-conjugated antibodies. The combination of an osmium or ruthenium labeled bead together with an additional tag of a metal-conjugated antibodies opens a variety of novel methods for control, compensation or quantification in mass cytometry assays including, but not limited to an assessment of channel crosstalk or absolute quantification of cell surface receptors/molecules as described herein.

In a further embodiment the invention relates to beads for use as a control, calibration and/or quantification probe in a mass cytometry assay or a method of analyzing beads as control, calibration and/or quantification probes in a mass cytometry assay as described herein, wherein the beads are labeled with a heavy metal, preferably osmium and/or ruthenium, and exhibit a surface functionalization allowing for the binding of an affinity reagent.

As used herein the "surface functionalization of the beads" refers to any chemical or biochemical modification of the surface of the beads that can mediate the binding of an affinity reagent. For instance, the surface functionalization may refer to the presence of capturing elements, e.g. capturing antigens, on the surface of the beads that display an affinity for affinity reagents, e.g. antibodies. The presence of capturing elements for an antibody constitutes an antibody capturing site. However, the surface functionalization may also refer to chemical or biochemical modification of the surface of the beads that allows for the binding of the capturing elements and thus the formation of antibody capturing sites. Different binding mechanisms for the capturing elements can be used including covalent chemical bonds or physical adsorption. A common method for the functionalization of polystyrene beads involves covalent attachment of the capturing elements to amine groups present at the surface (Schiro, P. G.; Kwok, A. S. Opt. Exp. 2004, 12, 2857-2863) for latex beads carboxyl groups may be used. However, also a functionalization of the surface of the beads using click chemistry as described in Dana R. et al. *Langmuir* 2009, 25(8), 4370-4376, may be envisioned.

Preferably the beads exhibiting a surface functionalization allowing for the binding of an affinity reagent refer to beads exhibiting antibody capturing sites mediated by capturing elements on their surface that have an affinity for a specific antibody. Such beads are also referred as antibody-capture beads. Commercial examples of antibody-capture beads comprising antibody capturing sites include BD™ CompBeads from BD Bioscience (Cat. No. 552844, 552843 or 552845), MACS Comp Bead from Miltenyi Biotec GmbH (Cat. No. 130-104-187, 130-097-900, 130-104-693, 130-107-755), AbC™ Total Antibody Compensation Bead Kit from ThermoFisher Scientific or Quantum™ Simply Cellular® from Bangslab (Cat. 815, 816 or 817).

In a preferred embodiment of the invention, the beads labeled with a heavy metal, preferably osmium and/or ruthenium, exhibit a surface functionalization that is characterized by the presence of antibody capturing sites.

Advantageously, these functionalized beads can thus bind antibodies, preferably metal-conjugated antibody such that the beads encompass two different mass tags. As a primary signal the beads can be distinguished in a mass cytometry assay based upon the heavy metal label and a secondary detection signal may stem from the metal-conjugated antibody that binds to the beads. As described herein, such functionalized and heavy metal labeled beads allow for novel methods for control, compensation or quantification in mass cytometry assays.

In a preferred embodiment, the invention relates to beads or a method of analyzing beads as control, calibration and/or quantification probes in a mass cytometry assay as described herein, wherein the beads are labeled with a heavy metal, preferably osmium and/or ruthenium as described herein, and that are in addition mass tagged with a metal-conjugated antibody on their surface.

In a preferred embodiment the beads are polymeric beads, preferably made of a polymer capable of a reaction with a tetroxide, most preferably polystyrene. The polymer may preferably be a synthetic or semisynthetic polymer. Examples of preferred polymers include polyacrylnitrile (PNA), melamine resin based polymers and/or polystyrene. It is preferred that the polymer is capable of a reaction with a tetroxide, preferably with a heavy metal tetroxide. Polymers suited to this end, are in particular polymers that exhibit aromatic structures and/or double bounds. A method to test whether a polymer is capable of a reaction with a tetroxide is to incubate a bead made from said polymer with a heavy metal tetroxide solution, preferably an osmium tetroxide solution as described herein and test the stable association of the heavy metal, preferably the osmium to the bead. For instance, the polymeric bead may be incubated with osmium textroxide diluted in PBS at a concentration of 0.01 wt.-% for 30 minutes. Stable association of the osmium with a polymeric bead over at least 1 week at 4° C. can be tested by determining the detection signal at time point zero and after one week as described above. If a decline of the detection signal of osmium in a mass cytometry assay is less than 50% a stable association is verified and the polymer is capable of a reaction with a tetroxide as meant herein.

In a further embodiment the invention relates to a method for labelling beads comprising the steps of
providing beads,
providing a heavy metal tetroxide diluted in a buffer solution, and
contacting (incubation of) the beads with the heavy metal tetroxide dilution.

In a further embodiment the invention relates to a method of analyzing beads as control, calibration and/or quantification probes in a mass cytometry assay as described herein, wherein the beads have been labeled by incubating the beads with a dilution of a heavy metal tetroxide selected from the group consisting of osmium tetroxide and ruthenium tetroxide in a buffer solution.

Surprisingly, such a simple incubation of the beads with heavy metal tetroxide results in a stable association of the heavy metal as a mass tag. The reliable labelling can be partially attributed to the high reactivity of the heavy metal tetroxide particularly with polymeric bead. As used herein the heavy metal tetroxide refers to a chemical compound of an oxidation state of the heavy metal in which four oxygen atoms bind to the heavy metal.

In a preferred embodiment the heavy metal tetroxide is selected from the group comprising osmium tetroxide and ruthenium tetroxide. Osmium tetroxide also termed osmium (VIII) oxide has the formula $OsO_4$ and ruthenium tetroxide (ruthenium(VIII) oxide) has the formula $RuO_4$. Both heavy metal tetroxides are the highest oxidation state (+8) of the metals.

In a further preferred embodiment, the concentration of the heavy metal tetroxide diluted in the buffer solution is in between 0.0001 wt.-% to 0.01 wt.-%, preferably 0.001 wt.-% to 0.01 wt.-%.

In a further preferred embodiment, the beads are incubated with the heavy metal tetroxide dilution for a time period between 1 min and 6 hours, preferably between 10 min and 4 hours, most preferably between 20 min and 1 hour.

These parameter ranges have proven to result in a particularly stable association of the heavy metals, such as osmium or ruthenium, to the beads for over a month at 4° C. Moreover, the concentration ranges yield a mass tag density that can be optimally detected in a mass cytometer.

In a further preferred embodiment of the invention the method is characterized in that the beads exhibit a surface functionalization allowing for the binding of an affinity reagent and that the step of providing the beads includes a step of providing beads labeled with the affinity reagent and/or the method further includes a step of labelling the beads with the affinity reagent and wherein the affinity reagent is preferably an antibody, most preferably a metal-conjugated antibody.

Preferably the surface functionalization is characterized by the presence of a capturing element for an antibody as described herein.

Surprisingly, the incubation of the beads with a heavy metal tetroxide does not interfere with the surface functionalization, e.g. capturing elements for antibodies remain intact and functional. Therefore, it is possible to first label the functionalized beads with a heavy metal such as osmium or ruthenium and afterwards stain the beads with a desired antibody, in particular a metal-conjugated antibody. It is even possible to first bind a metal-conjugated antibody to a surface functionalized bead and afterwards perform the labelling method with a heavy metal tetroxide. However, an order in which the functionalized beads are first labeled with a heavy metal and afterwards with the desired metal-conjugated antibody is preferred.

In a further embodiment the invention relates to beads producible or produced by the method for labeling beads with a heavy metal as described herein.

In a preferred embodiment the invention relates to the use of a bead as described herein in a mass cytometry assay, preferably for an assessment of channel crosstalk, for an absolute quantification of cell surface receptors and/or as a control for an assessment of instrument stability of a mass cytometer.

In preferred embodiments the method of analyzing beads as control, calibration and/or quantification probes in a mass cytometry assay, comprises an assessment of channel crosstalk, an absolute quantification of cell surface receptors or for an assessment of instrument stability of the mass cytometer in a mass cytometry assay.

In a preferred embodiment the invention relates to a method for the compensation of channel crosstalk and/or spill-over in a mass cytometry assay comprising
  providing a mass cytometer
  providing one or more groups of beads as described herein, wherein the one or more groups of beads are each further labeled by a type of metal-conjugated antibody
  providing cells incubated with the one or more types of metal-conjugated antibodies
  introducing said beads and said cells into the mass cytometer for an elemental analysis
  using data acquired from the beads for compensating channel-cross talk or spill-over in the data acquired from the cells.

The embodiment thus preferably encompasses performing a mass cytometry assay by introducing said beads and said cells into the mass cytometer for an elemental analysis, wherein data acquired from said beads is used for compensating channel-cross talk or spill-over in the data acquired from said cells.

The step of providing a mass cytometer preferably included the provision of a mass cytometer as described herein comprising a sample introduction system for introducing cells or beads sequentially and an ion-source, such as an inductively coupled plasma ionization source, coupled to a mass cytometer. Advantageously commercially available mass cytometers such as the CyTOF, CyTOF2, and Helios (CyTOF3) systems by Fluidigm can be used without the need of any adaptation.

The step of provision of one or more groups of beads, wherein the one or more groups of beads are each further labeled by a type of metal-conjugated antibody may comprise steps to produce such beads. For instance, one or more groups of functionalized beads exhibiting antibody capturing sites may be provided and subsequently labeled with a heavy metal preferably selected from a group comprising osmium and/or ruthenium as described herein.

Advantageously, such functionalized beads exhibiting antibody capturing sites are readily available. Commercial examples include BD™ CompBeads from BD Bioscience (Cat. No. 552844, 552843 or 552845), MACS Comp Bead from Miltenyi Biotec GmbH (Cat. No. 130-104-187, 130-097-900, 130-104-693, 130-107-755), AbC™ Total Antibody Compensation Bead Kit from ThermoFisher Scientific or Quantum™ Simply Cellular® from Bangslab (Cat. 815, 816 or 817). The labelling with a heavy metal, for instance by incubating with a heavy metal tetroxide advantageously does not interfere with the functionalization.

Thus, the one or more groups of beads exhibiting antibody capturing sites—additionally labeled with a heavy metal—can be stained with metal-conjugated antibodies. Again, advantageously a variety of metal-conjugated antibodies for mass cytometry assay are commercially available including for instance the MaxPar reagents from Fluidigm.

Preferably the types of metal-conjugated antibodies are chosen according to desired experimental setup for an assessment of cellular parameters. For instance, if cell surface receptors such as CD4, CD16 or CD20 are to be measured commercially available metal-conjugated antibodies such as CD4-Nd144 antibodies or CD20-Sm147 antibodies may be used. As used as nomenclature herein for the metal-conjugated antibodies, the first part denotes the affinity of the antibody, e.g. for the receptors CD4 or CD20 and the second part denotes the metal-conjugation mediated mass tag, e.g. Neodymium (Nd) with an MW of 144 or Samarium (Sm) with an MW of 147. For such an experimental setting, it is preferred that for each type of metal-conjugated antibody (e.g. CD4-Nd144 or CD20-Sm147) a group of heavy metal labeled beads is provided that is additionally tagged or labeled with said type of metal-conjugated antibody.

After introducing the cells incubated with the metal-conjugated antibodies into a mass cytometer the signal detected from the metal mass tag, e.g. Nd144 or Sm147) allows for an assessment of the presence of the corresponding receptors, e.g. CD4 or CD20, on each individual cell.

The inventors have realized however that the signal of a certain metal-conjugated antibodies, e.g. stemming from the Nd144 mass tag, does not only accumulate in the assigned detection channel corresponding to molecular weight "144" as it should be the case for ideal instrumentation and mass tags. Instead, isotopic impurities, oxidation or other reason may lead to a spilling over of signals into adjacent channels. The signal detected in a specific detection channel representing a molecular weight may thus include signals from adjacent channels. Such a channel crosstalk can interfere with a correct data interpretation.

According to the method described herein, one or more groups of beads labeled with the metal-conjugated antibodies are introduced sequentially or simultaneously with the cells. A simultaneous introduction of beads and cells may preferably be achieved by mixing the beads with cells and introducing the mixture into the mass cytometer for an elemental analysis, The sequentially or simultaneously introduced beads may also be referred to as compensation beads. Advantageously, based upon the heavy metal signal e.g. osmium and/or ruthenium, the beads can be readily distinguished in the mass cytometer. Since each detected compensation bead will only be stained with exactly one type of metal-conjugated antibody, the detection signals from the compensation beads allow for an accurate quantification of the spill-over or channel crosstalk. Based on the data of the heavy metal labeled compensation beads a spill-over matrix can be calculated that represents the spill-over or crosstalk from a certain metal-conjugated antibody into adjacent detection channels (see e.g. FIG. 10c for an example of a spill-over matrix). The spill-over matrix can be used to compensate for channel crosstalk in the detected signals stemming from cellular events. To this end, linear or non-linear compensation algorithms may be used that take into account the actual detection profile of a metal-conjugated antibody in the mass cytometer as derived from the bead data and calculate for each cellular event an adjusted signal.

Since the compensation beads are introduced at the same time, such a compensation is particularly accurate and allows even for a time dependent compensation taking into account any kind of time-dependent variety in instrumentation stability.

Such a compensation strategy may be particularly valuable for clinical diagnostic assays in which a multitude of metal-conjugated antibodies are used for a comprehensive parameterization of cells. Currently more than 40 metal-conjugated antibodies have been used in such assays. The more metal-conjugated antibodies are used the more likely a crosstalk or signal spill-over may compromise the data interpretation. The methods and beads disclosed herein are thus particularly suited for such applications.

In a further preferred embodiment, the invention relates to a kit for performing a method as described herein, either for producing the beads described or carrying out an analytical mass cytometry method. The kit preferably comprises beads for use as a control, calibration and/or quantification probe in a mass cytometry assay, as described herein, together with a heavy metal selected from the group comprising osmium or ruthenium, provided in a form suitable to label said heavy metal to said beads, preferably in form of a osmium or ruthenium tetroxide solution.

In a further preferred embodiment the invention relates to a kit for performing a method for the compensation of channel crosstalk or spill-over in a mass cytometry assay as described herein, comprising a panel of beads comprising multiple groups of beads labeled with a heavy metal preferably selected from osmium or ruthenium as described herein, wherein each group of beads is further labeled with a different type of metal-conjugated antibody and wherein the number of groups of beads corresponding to different types of metal-conjugated antibodies represented by the panel is greater than 5, preferably greater than 10, most preferably greater than 20. The kit may further comprise instructions for performing said compensation method as described herein.

The kit is thus characterized in that a panel of compensation beads is provided comprising for each group two defined mass tags, one from the heavy metal label and a second one from a certain metal-conjugated antibody. The panel of compensation beads may thus represent as a reference library for a panel of metal-conjugated antibodies that are commonly used in mass cytometry assays. The panel of compensation beads can be tailored to certain experimental setups or clinical assay. The provision of the kit with a ready to apply panel of compensation beads is particular user friendly and suited as standard compensation control in a variety of mass cytometry assays.

In a further embodiment the invention relates to a computer program configured for determining data produced from the mass cytometry analysis of the beads as described herein. Such computer programs may be configured by an appropriately skilled person, in knowledge of the heavy-metal labelling described herein.

In preferred embodiments the computer program comprises instructions which, when the program is executed by a computer, causes the computer to detect the heavy metal label selected from the group consisting of osmium or ruthenium of the beads and to analyze the data acquired from said beads for an assessment of channel crosstalk, for an absolute quantification of cell surface receptors or for an assessment of instrument stability of the mass cytometer.

In a further embodiment the invention relates to a computer program for use in a method for the compensation of channel crosstalk or spill-over in a mass cytometry assay as described herein comprising instructions which, when the program is executed by a computer, cause the computer to carry out steps of analyzing the data acquired from each of the one or more groups of beads labeled by a different type of metal-conjugated antibody to create a spill-over matrix containing information on the signal spill-over from the different types of metal-conjugated antibodies into adjacent detection channels of the mass cytometer and using the spill-over matrix to compensate for channel-crosstalk in the data acquired from the cells.

The computer program allows for an automated analysis of the signals obtained from the compensation beads to create a spill-over matrix, which can be used to automatically compensate for channel-crosstalk in the data acquired on cellular events. In a preferred embodiment the computer program may be part of the kit comprising the panel of compensation beads.

In a further preferred embodiment, the invention relates to a method for an absolute quantification of cell surface receptors comprising Providing of a mass cytometer, Providing at least two groups of beads as described herein, wherein the beads of each of the at least two groups exhibit a different defined amount of antibody capturing sites and are labeled with a different defined amount of a heavy metal preferably selected from the group comprising osmium or ruthenium, Providing cells, Incubating the cells with a type of metal-conjugated antibody targeting a cell surface receptor, Incubating the least two groups of beads with the same type of metal-conjugated antibody under saturating conditions, Mixing of said beads with said cells and introduction of the mixture into the mass cytometer for an elemental analysis, Calculating a reference curve from the data acquired from the at least two groups of beads yielding a correlation between signal intensity detected in a mass cytometer and absolute amount of metal-conjugated antibodies, and Using said reference curve for an absolute quantification of cell surface receptors Using conventional mass cytometry, it is possible to assess the distribution of a multitude of cell surface receptors for individual cells at the same time. A strategy for an absolute quantification of the number or density of cell surface receptors has however been missing. The labelling of surface functionalized beads with a heavy metal preferably osmium or ruthenium fills this gap and allows for an absolute quantification using the method disclosed herein.

The step of providing the at least two groups of beads, wherein the beads of each of the at least two groups exhibit a different defined amount of antibody capturing sites and are labeled with a different defined amount of a heavy metal preferably selected from the group comprising osmium or ruthenium may comprise the production of such beads. For instance, the at least two groups of functionalized beads exhibiting different defined amounts of antibody capturing sites may be provided and subsequently labeled with a heavy metal preferably selected from a group comprising osmium and/or ruthenium as described herein.

Such functionalized beads exhibiting a defined amount of antibody capturing sites are commercially available. For instance, to this end Quantum™ Simply Cellular quantification beads from Bangs Laboratories Inc. designed for the calibration in fluorescence-based flow cell cytometry may be used. As shown in FIG. 8 five population characterized by a defined amount of binding sites can be chosen e.g. 0, 12'391, 65'076, 249'738 and 814'348. In order to label each of the group of beads with a defined amount of heavy metal, e.g. osmium, the beads exhibiting the antibody capturing sites can be incubated for instance in a labelling method as described herein with distinct concentrations of osmium tetroxide (e.g. 0.0001 wt.-%, 0.001 wt.-%, 0.0025 wt.-%, 0.0005 wt.-% or 0.01 wt.-% see FIG. 8).

Subsequently the heavy metal labeled beads carrying defined amounts of antibody capturing sites are incubated at saturating conditions with a metal-conjugated antibody. The saturating condition ensures that the amount of metal-conjugated antibodies binding to the beads corresponds to the known and defined amount of antibody capturing sites.

The cells are equally incubated with the metal-conjugated antibody that has an affinity for a desired cell surface receptor. For instance, if the receptor density of CD4 is to be determined a CD4-Nd144 antibody may be used. In a conventional mass cytometry assay the cells are introduced and the signal stemming from the Nd144-mass tag will allow for a relative quantification of the expression of CD4 in different cells. A translation of the signal into absolute numbers has not been possible. To this end the beads allow for the calculation of a reference or calibration curve. Since each group of beads is characterized by a defined amount of bound metal-conjugated antibodies and heavy metal label (e.g. osmium) the different groups of beads can be reliable identified in a mass cytometry.

Therefore, the known number of metal-conjugated antibodies bound to a bead and the signals detected from the metal-conjugated antibody of said bead can be correlated to yield a reference or calibration curve. It may be preferred that a linear correlation coefficient is assessed. Based upon the signal detected from a certain cell, the amount of metal-conjugated antibody bound to said cell can thus be determined in absolute numbers using the reference or calibration curve.

Advantageously, due to a strong primary signal stemming e.g. from an osmium-label the beads can be reliably separated from cellular events. This is particularly valuable for the group of beads that possess a relatively low number of metal-conjugated antibodies bound. Without the primary signal these beads would not be able to be identified based on the signal of the metal-conjugated antibody alone. The method however allows for the calculation of a particularly precise reference curve stemming from different groups of beads representing the relevant span of signals. As such the method thus enables for an absolute quantification of cell surface receptor density or amount with unprecedented accuracy. Such absolute quantification can be particularly beneficial for the comparison and integration of large data sets stemming from different experimental setting as it is the case e.g. in clinical studies.

In a further embodiment the beads labelled with a heavy-metal preferably selected from a group comprising osmium or ruthenium are used to serve as a channel and/or reagent-specific reference for signal drift that cannot or not fully be corrected by the use of commercially available normalization beads.

BRIEF DESCRIPTION OF THE DRAWINGS

The invention is further described by the following figures. These are not intended to limit the scope of the invention, but represent preferred embodiments of aspects of the invention provided for greater illustration of the invention described herein.

DETAILED DESCRIPTION

Figure 1:
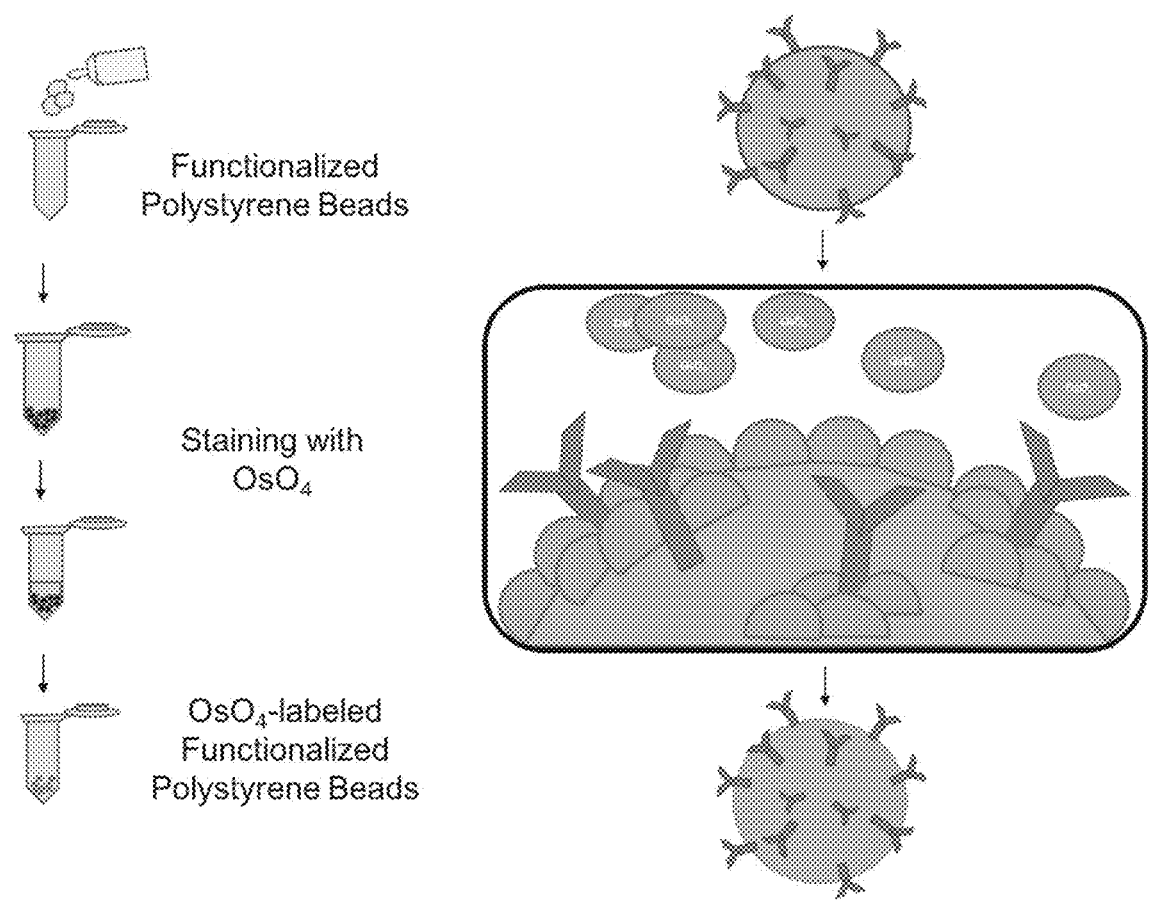
FIG. 1: Scheme for the osmium tetroxide labelling of functionalized beads. Labelling is achieved by co-incubation of beads with highly diluted OsO4 in PBS.

The present invention is directed to the beads labelled with a heavy metal preferably select from a group comprising osmium and ruthenium as well as their use for a control, compensation or quantification in mass cytometry assays. Before the present invention is described with regards to the examples, it is to be understood that the terminology used herein is for the purpose of describing particular embodiments only and is not intended to limit the scope of the present invention.

As used herein the term "osmium" refers to the known chemical element with the symbol Os and an atomic number of 76. The term osmium shall encompass all isotopes of the element including $^{184}Os$, $^{85}Os$, $^{186}Os$, $^{187}Os$, $^{188}Os$, $^{189}Os$, $^{190}Os$, $^{191}Os$, $^{192}Os$, $^{193}Os$ and/or $^{194}Os$, preferably $^{186}Os$, $^{187}Os$, $^{188}Os$, $^{189}Os$, $^{190}Os$, and/or $^{192}Os$. A bead labeled with osmium may thus refer to a bead labeled with the element, a specific isotope or any combination of isotopes of osmium.

As used herein the term "ruthenium" refers to the known chemical element with the symbol Ru and an atomic number of 76. The term "ruthenium" shall encompass all isotopes of the element including $^{96}Ru$, $^{97}Ru$, $^{98}Ru$, $^{99}Ru$, $^{100}Ru$, $^{101}Ru$, $^{102}Ru$, $^{103}Ru$, $^{104}Ru$, $^{105}Ru$ and/or $^{106}Ru$ preferably $^{96}Ru$, $^{98}Ru$, $^{99}Ru$, $^{100}Ru$, $^{101}Ru$, $^{102}Ru$ and/or $^{104}Ru$. A bead labeled with ruthenium may thus refer to a bead labeled with the element, a specific isotope or any combination of isotopes of ruthenium.

As used herein the term "heavy metal" includes any metal with a density of 4 $g/cm^3$ or more, preferably 5 $g/cm^3$ or more. The term heavy metal may thus encompasses Antimony, Cerium, Dysprosium, Erbium, Europium, Gadolinium, Gallium, Germanium, Holmium, Iodine, Indium, Lanthanum, Lutetium, Neodymium, Niobium, Praseodymium, Samarium, Tantalum, Terbium, Thulium, Tungsten, Uranium, Ytterbium, Iridium, Osmium, Palladium, Platinum, Rhodium, Ruthenium, Gold, Silver, Chromium, Cobalt, Copper, Iron, Lead, Molybdenum, Nickel, Tin, Zinc, Arsenic, Bismuth, Cadmium, Hafnium, Manganese, Mercury, Protactinium, Rhenium, Selenium, Tellurium, Titanium, Thallium, Thorium, Vanadium, Yttrium, Zirconium, Actinium, Americium, Berkelium, Californium, Curium, Dubnium, Einsteinium, Fermium, Mendelevium, Neptunium, Plutonium, Polonium, Promethium, Radium, Technetium, Astatine, Bohrium, Copernicium, Darmstadtium, Flerovium, Hassium, Lawrencium, Livermorium, Meitnerium, Moscovium, Nihonium, Nobelium, Roentgenium, Rutherfordium, Seaborgium, Tennessine.

Preferred heavy metals refer to heavy metals elements or isotopes having a molecular weight between 70 and 215, preferably between 75 and 209. Preferably the heavy metals are a metallic solid at standard conditions. Furthermore it is preferred that a heavy metal element us used herein can form a reactive oxide, such as a tetroxide, for example with analogous function to osmium tetroxide.

The terms "antibodies" and "immunoglobulin" include antibodies or immunoglobulins of any isotype, fragments of antibodies which retain specific binding to antigen, As used herein, the terms antibody and immunoglobulin are used interchangeably and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions. The term antibody covers monoclonal antibodies (including full-length monoclonal antibodies), polyclonal antibodies, multispecific antibodies (e.g., bispecific antibodies), fusion proteins comprising an antigen-binding portion of an antibody and a non-antibody protein and antibody fragments so long as they exhibit the desired biological activity.

"Antibody fragments" comprise a portion of a full-length antibody, generally the antigen binding or variable region thereof. Examples of antibody fragments include Fab, Fab', F(ab')2, and Fv fragments; diabodies; linear antibodies; single-chain antibody molecules; and multispecific antibodies formed from antibody fragments. Preferred antibody fragments may include fragments derived from an enzymatic digestion or a chemical reduction, for instance using TCEP (tris(2-carboxyethyl)phosphine). The antibodies may be detectably labeled, e.g., with a radioisotope, an enzyme which generates a detectable product, a fluorescent protein, a fluorescent molecule, or a stable elemental isotope and the like.

As used herein a "metal-conjugated antibody" refers to an antibody to which a metal as a mass tag is conjugated. Examples of commercially available metal-conjugated antibodies include Maxpar Reagents catalog of Fluidigm comprising more 600 entries (http://maxpar.fluidigm.com/product-catalog-metal.php).

As used herein, the term "mass tagged" refers to a molecule that is tagged with either a single kind of stable isotope that is identifiable by its unique mass or mass profile or a combination of the same, where the combination of stable isotopes provides an identifier. Combinations of stable isotopes permit channel compression and/or barcoding. Examples of elements that are identifiable by their mass include heavy metals. An element may exist as one or more isotopes, and this term also includes isotopes of positively and negatively metals. The terms "mass tagged" and "elementally tagged" may be used interchangeably herein.

As used herein, the term "mass tag" means any isotope of any element, including heavy metals that is identifiable by its mass, distinguishable from other mass tags, and used to tag an affinity reagent or a bead. A mass tag has an atomic mass that is distinguishable from the atomic masses present in the analytical sample and in the particle of interest. The term "monoisotopic" means that a tag contains a single type of metal isotope (although any one tag may contain multiple metal atoms of the same type).

As used herein, the term "elemental analysis" refers to a method by which the presence and/or abundance of elements of a sample are evaluated. The term elemental analysis shall also include analysis of isotopic composition and thus encompasses a mass analysis identifying mass tagged molecules using a mass cytometer as known in the art.

As used herein, the term "inductively coupled plasma" (ICP) means a source of atomization and ionization in which a plasma is established in an inert gas (usually argon) by the inductive coupling of radiofrequency energy. The frequency of excitation force is in the MHz range.

As used herein, the term "plasma source" means a source of atoms or atomic ions comprising a hot gas (usually argon) in which there are approximately equal numbers of electrons and ions, and in which the Debye length is small relative to the dimensions of the source.

As used herein, the term "flow cell" refers to a conduit in which particles flow, in a medium, one by one in single file.

As used herein, the term "polymer" preferably refers to a molecule consisting of individual chemical moieties, which may be the same or different, but are preferably the same, that are joined together. As used herein, the term "polymer" refers to individual chemical moieties that are joined end-to-end to form a linear molecule, as well as individual chemical moieties joined together in the form of branched structures.

The term "affinity reagent" preferably refers to one member of a binding pair, wherein the term "binding pair" includes any of the class of immune-type binding pairs, such as antigen/antibody or hapten/anti-hapten systems; and also any of the class of nonimmune-type binding pairs, such as biotin/avidin; biotin/streptavidin; folic acid/folate binding protein; lectin/sugar; lectin/glycoprotein complementary nucleic acid segments; protein A or G/immunoglobulins; and binding pairs which form covalent bonds, such as sulfhydryl reactive groups including maleimides and haloacetyl derivatives, and amine reactive groups such as isotriocyanates, succinimidyl esters and sulfonyl halides.

The term "capturing element" preferably refers to the second member of a binding pair capable of binding to an affinity reagent. Preferably the "capturing element" is capture antigen directed to the binding of an antibody.

An "antibody capturing site" refers to a surface group on the surface of the bead where antibodies are specifically captured or bound the "antibody capturing site" is therefore referred to as an antibody binding site. An antibody capturing site is distinct however from a site on the surface of the bead that only allows for an unspecific attachment of an antibody. Preferably the "antibody capturing site" is formed by capturing elements that specifically target an antibody.

As used herein, the term "buffer solution" is refers to an aqueous solution in which the heavy metal tetroxide is solved. The aqueous solution may contain a miscible organic solvent, such as Tetrachlormethan, Ethanol, Diethylether und Benzol and a buffer to control the pH of the solution. Examples of suitable buffers solutions include but are not limited to PBS (phosphate buffered saline), TRIS (tris-(hydroxymethyl)aminomethane), HEPES (hydroxyethylpiperidine ethane sulfonic acid), and TES 2-[(tris-hydroxymethyl)methyl]amino-1-ethanesulfonic acid. The buffer solution is chosen for the heavy metal tetroxide. For instance for ruthenium tetroxide is may be preferred that the buffer solution Carbon tetrachloride (CCL4).

"Cell surface receptors" are molecules anchored on the cell plasma membrane. They constitute a large family of proteins, glycoproteins, polysaccharides and lipids, which serve not only as structural constituents of the plasma membrane, but also as regulatory elements governing a variety of biological functions. As a protein a cell surface receptor is expressed on the surface of a cell and typically include a transmembrane domain or other moiety that anchors it to the surface of a cell. As a receptor it binds to ligands that mediate or participate in an activity of the cell surface receptor, such as signal transduction or ligand internalization. Cell surface receptors include, but are not limited to, single transmembrane receptors and G-protein coupled receptors. Receptor tyrosine kinases, such as growth factor receptors, also are among such cell surface receptors.

As used herein the terms "spill-over" or "channel crosstalk" refers to the phenomena that in a mass cytometry assay the signal of a certain metal-conjugated antibody does not only produce a signal in its respective detection. Instead due to isotopic impurities, oxidation or other reason the signals stemming from said metal-conjugated antibody may "spill-over" into adjacent channels. The resulting channel crosstalk interferes with correct data interpretation.

As used herein the term "detection channel" or "channel" refers to defined portion of the data acquired by a mass cytometer in which signals representing a certain molecular weight are integrated. Typically mass cytometers exhibit a total range for the detection of a molecular weight of 75-209. With a width of a detection of one MW the entire acquired data may thus be portioned into 134 separate detection channels.

All cited documents of the patent and non-patent literature are hereby incorporated by reference in their entirety.

EXAMPLES

The invention is further described by the following examples. These are not intended to limit the scope of the invention, but represent preferred embodiments of aspects of the invention provided for greater illustration of the invention described herein.

The examples show that surface functionalized beads can be stably labeled with Osmium and successfully used in mass cytometry assays for instance for absolute cell receptors quantification or as compensation means for channel crosstalk.

Materials and Methods Used in the Examples:

Bead Labeling with OsO4

1 wt.-% osmium tetroxide solution was diluted in PBS to generate staining solutions ranging from 0.01-0.0001 wt.-%. Stocks were stored in brown glass vials at −80° C., working solutions in brown glass vials at −20° C.

Prior to osmium tetroxide staining polystyrene beads were pelleted by centrifugation (centrifugation according to manufacturer manual ranging between 1500 to 3000×g) and storage buffer removed by aspiration. For osmium staining, beads were resuspended in 20 µL of osmium tetroxide solution per $1 \times 10^6$ beads and incubated for 30 minutes at room temperature. After incubation, 1 mL PBS/BSA was added, beads were pelleted and supernatant was discarded ("washing"). Samples were washed at least three times with 1 mL PBS/BSA to remove unbound osmium tetroxide. The beads were then available for further staining protocols or resuspended in Millipore water for direct acquisition at the CyTOF instrument.

Antibody Conjugation

Metal-conjugated antibodies were purchased from Fluidigm (South San Francisco, Calif., USA), or produced in-house using the MAXPAR® X8 conjugation kit as per manufacturer's instructions. Unconjugated antibodies were isolated from hybridomas maintained at the DRFZ, or purchased from e.g. Biolegend (San Diego, Calif., USA), BD Biosciences (San Diego, Calif., USA), Miltenyi Biotech (Bergisch-Gladbach, Germany) and R&D (Minneapolis, Minn., USA).

Labeling of antibodies with palladium isotopes was carried out as described before using isothiocyanobenzyl-EDTA (Dojindo laboratories, Kumamoto, Japan) (Mei et al. *J Immunol.* 194 (2015)), with the adjustment that labeling was performed in PBS/2×Hepes/EDTA buffer. Antibody labeling using cisplatin was performed as described before (Mei et al. *Cytometry* A. 89, 2016). Metal salts not available through Fluidigm were purchased from Sigma (St. Louis, Mo., USA) or Trace Sciences (Richmond Hill, ON, Canada).

Preparation of PBMC

PBMC were prepared from fresh anticoagulated whole blood or from buffy coats by density gradient centrifugation over Ficoll (GE Healthcare, Chicago, Ill., USA) as described before (Schulz et al, *Cytometry* A. 91, 2017), washed in PBS/BSA, counted and frozen in FBS/10% DMSO according to standard procedures for longer-term storage in the vapor phase above liquid nitrogen. For each experiment, PBMC were thawed at 37° C., transferred to 50 mL pre-warmed RPMI 1640 supplemented with 10% FBS and 5 U/mL benzonase. To counteract metabolic activity, PBMC were immediately pelleted for 10 min at 500×g and 4° C. PBMC were washed once in 15 mL cool PBS (500×g, 4° C.) and counted at a MACSQUANT flow cytometer (Miltenyi). Finally, PBMC were resuspended in PBS and kept on ice for further use.

Figure 11:
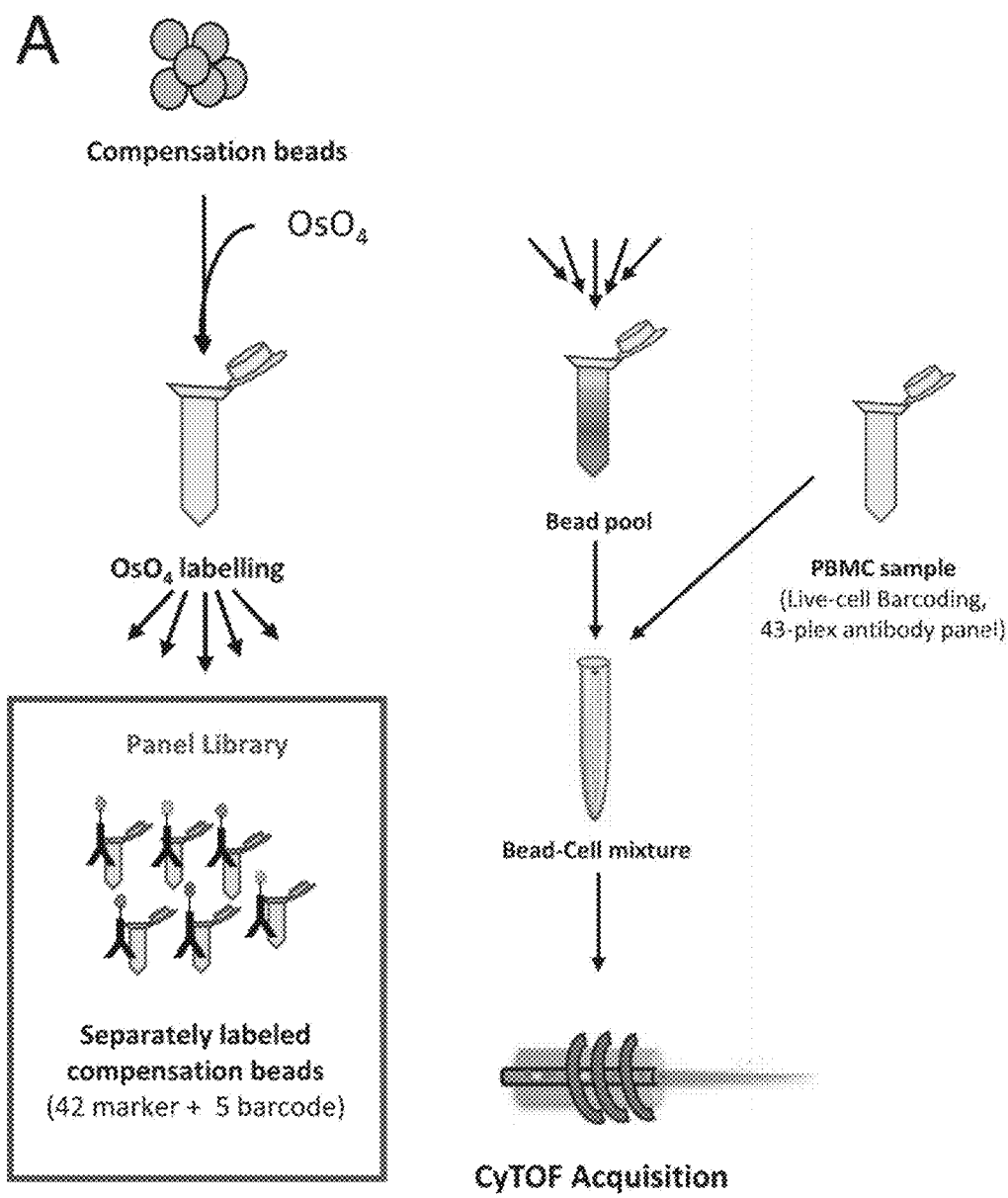
FIG. 11: Osmium labeling facilitates joint acquisition of cells and Ab capture beads for spillover correction. (A) Ab capture beads were first labeled with $OsO_4$, split into aliquots, which were individually stained with 47 different Ab conjugates of an Ab panel for analyzing PBMC. All beads were pooled and combined with PBMC stained with the same Ab panel for acquisition by the mass cytometer. Compensation with osmium-labeled beads was performed four times; for two (BO, B1), the applied panel is indicated. (B) Osmium-labeled beads were always discriminable from nucleated, iridium—DNA intercalator—labeled cells. $Os^+Ir^+$ events represent bead/cell doublets. t-SNE graphs of all bead pools (top) and CD45+ BMC (bottom) are shown. Colors indicate $^{113}In$ or $^{115}In$ signals prior to spillover correction (from blue, no signal to red, high signal). Note that the $^{113}In$ preparation used in the CD20 Ab conjugate contains 6.9% $^{115}In$ (according to the manufacturer), explaining the spillover detectable in the $^{115}In$ channel (used for detection of CD3) at the example of beads and PBMC. Compensation with osmium-labeled beads acquired simultaneously with cells was conducted two times. The spillover correction is shown for the panel referred to as B1. (C) Catalyst was used to calculate a spillover matrix based on bead data acquired together with cells. After signal correction (compensation) according to the calculated spillover matrix, beads that had captured the CD20 Ab conjugate and CD20+ B cells show the expected absence of a CD3 signal, as indicated by the blue color of the indicated populations. t-SNE maps were generated based on signal of all markers except barcoding channels and CD3– $^{115}In$. The data shown refer to one compensation experiment with osmium-labeled beads and cells stained with panel B1. (D) Bivariate plots of the same data shown in (B and C) before and after compensation.
Figure 11:
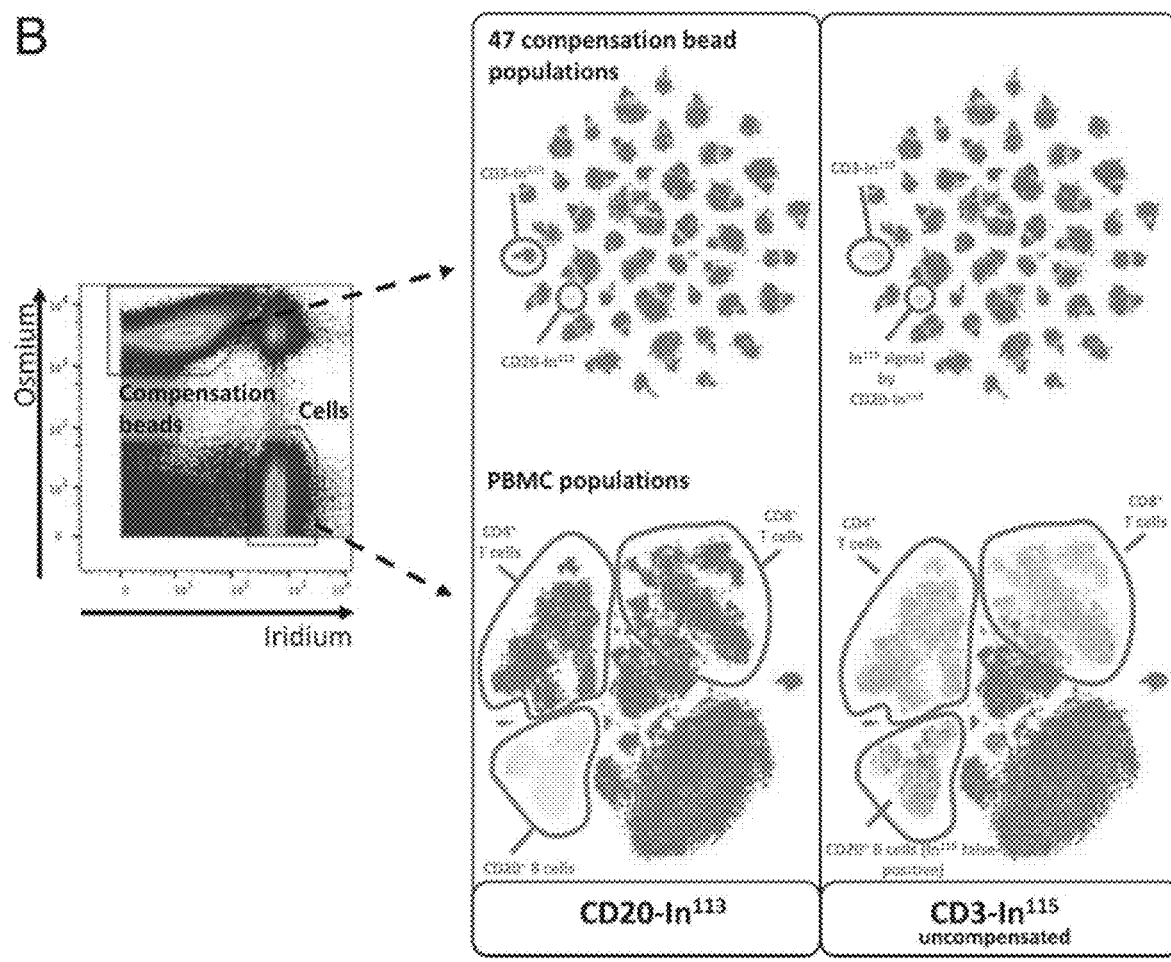
Figure 11:
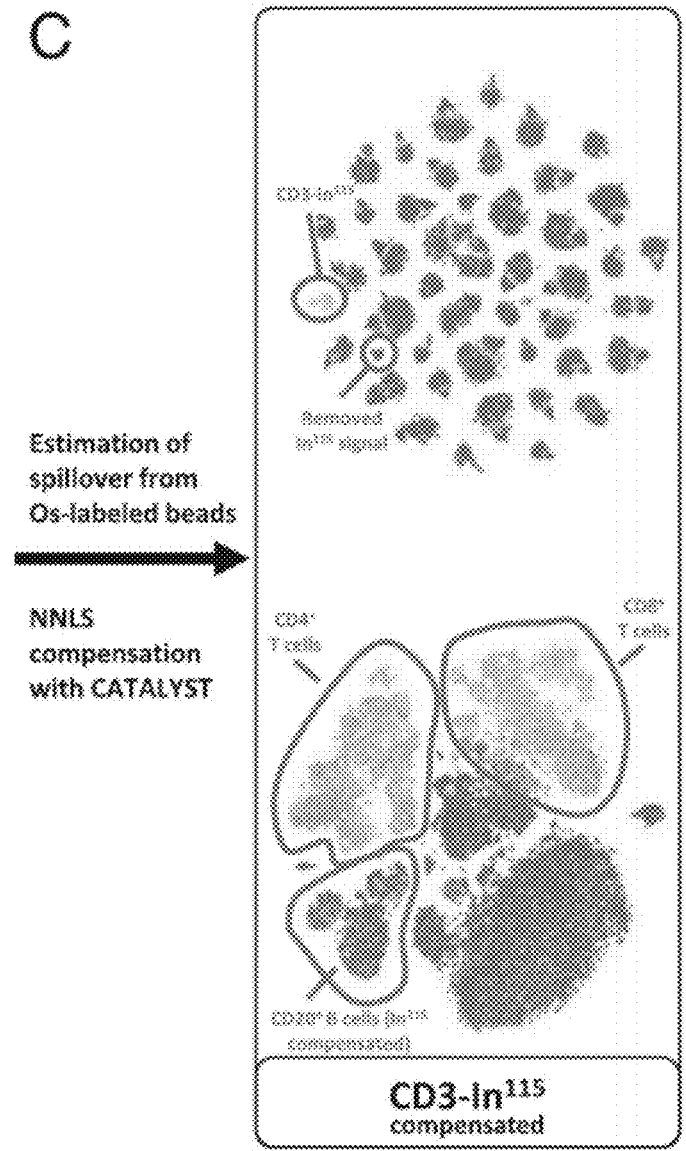
Figure 11:
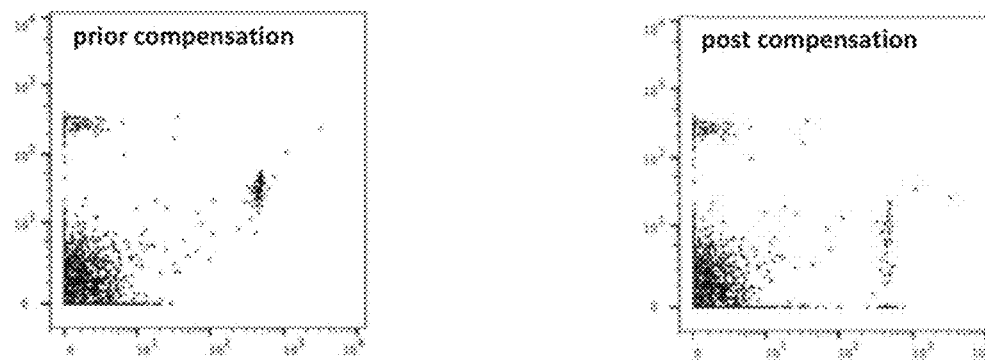
Figure 11:
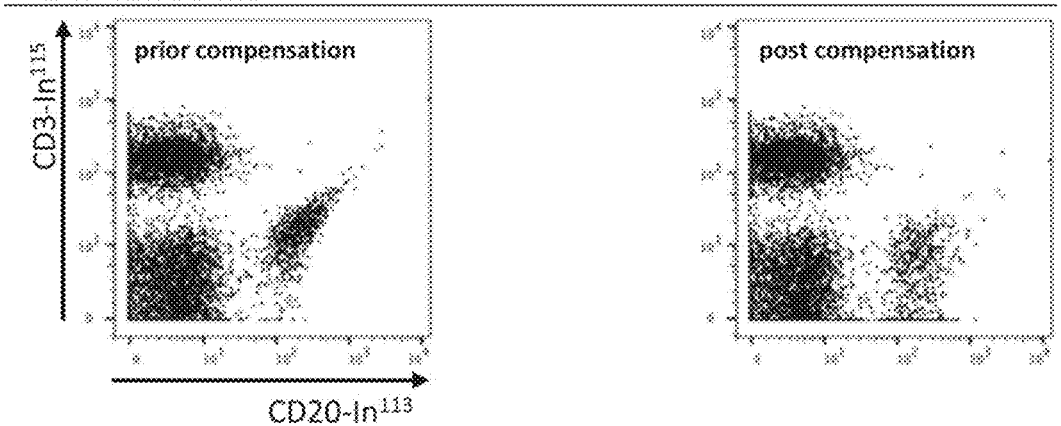

For the data depicted in FIG. 11 peripheral blood samples were drawn by venipuncture from healthy individuals and patients diagnosed with SLE or inclusion body myositis under approval by the local ethic committees in accordance with the Helsinki Declaration (approval identifier EA1/132/116). All donors gave written informed consent prior to blood donation. For some experiments PBMC were isolated from buffy coats obtained from the Institute of Transfusion Medicine, Charite University Medicine, Berlin, Germany. PBMCs were prepared from anticoagulated whole blood samples by density gradient centrifugation using Ficoll (800×g, 20 min; GE Healthcare; Chicago, Ill.). PBMC were subsequently washed twice in 45 ml of CSM, counted by volumetric flow cytometry (MACSQuant; Miltenyi).

Preparation of PBMC for Mass Cytometry

Antibody cocktails were prepared in PBS/BSA as diluent on ice. For staining cell-surface antigens, up to 2×10$^6$ PBMC were resuspended in 50 µL antibody cocktail and incubated for 30 min at 4° C. in 1.5 mL Eppendorf vials (Eppendorf, Hamburg, Germany). Cells were pelleted (500×g, 4° C., 5 min), the supernatant aspirated, and resuspended 1 mL 800 nM mDOTA-Rh103 solution (diluted in PBS) for 5 min at room temperature (RT), to label dead cells for their latter exclusion from mass cytometry data. The sample volume was topped up with 500 µL PBS/BSA followed by cell pelleting and supernatant aspiration. The cells were washed once with 1 mL PBS/BSA, once in 1 mL PBS, and finally resuspended in 2% PFA solution (diluted from 16% stock with PBS) and incubated at 4° C. overnight.

On the next day, 500 µL PBS/BSA were added, and cells were pelleted at 700×g, 5 min, 4° C. Cells were washed once with 1 mL PBS/BSA, and were then incubated for 25 min at room temperature (RT) in 500 µl permeabilization buffer supplemented with iridium-based DNA intercalator. Cells were then washed twice with 1 mL PBS/BSA. Thereafter, samples were resuspended in 1 mL PBS and counted on a MACSQUANT flow cytometer. Prior to acquisition on the CyTOF instrument, samples were washed twice with 500 µl Millipore water and pelleted by centrifugation at 800×g, 5 min, 4° C. Cells were then resuspended in an appropriate volume of water supplemented with EQ 4 element beads and were optionally filtered through 35 µm cell strainer cap tubes (BD, San Jose, Calif., USA,) prior to acquisition.

Cell-surface barcoding was employed as described before (Mei et al. *Cytometry* A. 89, 2016).

Mass Cytometry

Mass cytometry was performed on CyTOF version 1 (operating as described before (Schulz et al, *Cytometry* A. 91, 2017, Baumgart et al. *Cytometry* A. 91) and Helios instruments (Fluidigm). Instruments were daily prepared for acquisition by tuning and cleaning according to the manufacturer's advice, using tuning and cleaning solutions (Fluidigm). Data of cells or bead suspensions were acquired in cell acquisition mode at event densities of $<5\times10^5$ events/mL for CyTOF v1 and $<7.5\times10^5$ events/mL for the Helios instrument.

The sample supply was set to 45 µL/min for CyTOF v1, or to 35 µL/min for the Helios instrument. Both instruments were run in dual calibration mode, with noise reduction turned on and event length thresholds set to 10 and 75. The lower limit was set to 3 in some detection limit experiments.

Antibody Capture Beads for Ab Conjugate Quality Control and Compensation

For antibody capturing, antibody capture beads from different sources were processed with a protocol similar to that used for cell-surface staining of PBMC. Briefly, aliquots of up to 2×10$^6$ beads were stained in 50 µL PBS/BSA containing a single antibody conjugate (applied in the similar volume ratio as for cell surface staining; optimal dilution determined with 1-2×10$^6$ PBMC) for 30 min at 4° C. Then, beads were washed three times in 1 mL PBS/BSA, and finally resuspended and incubated in 500 µL 2% paraformaldehyde solution overnight at 4° C. Fixation was stopped by adding 500 µL PBS/BSA followed by centrifugation and aspiration of supernatant. Finally, beads were washed twice in PBS/BSA, once in PBS, and once in water.

For the experiment shown in FIG. 11, a large batch of beads was labeled with osmium tetroxide, aliquoted into cavities of a 96-well Deep Well Plate (Corning, Corning, N.Y.), and incubated with individual Ab conjugates. After loading of beads with Ab conjugates and washing, bead aliquots were pooled and either stored at −80° C. or directly combined with cell suspensions previously stained with Intercalator-Ir and the same set of isotope-tagged Abs (1:4, v/v) for simultaneous acquisition.

Experimental Setup for Mass Cytometry Data Compensation

Figure 8:
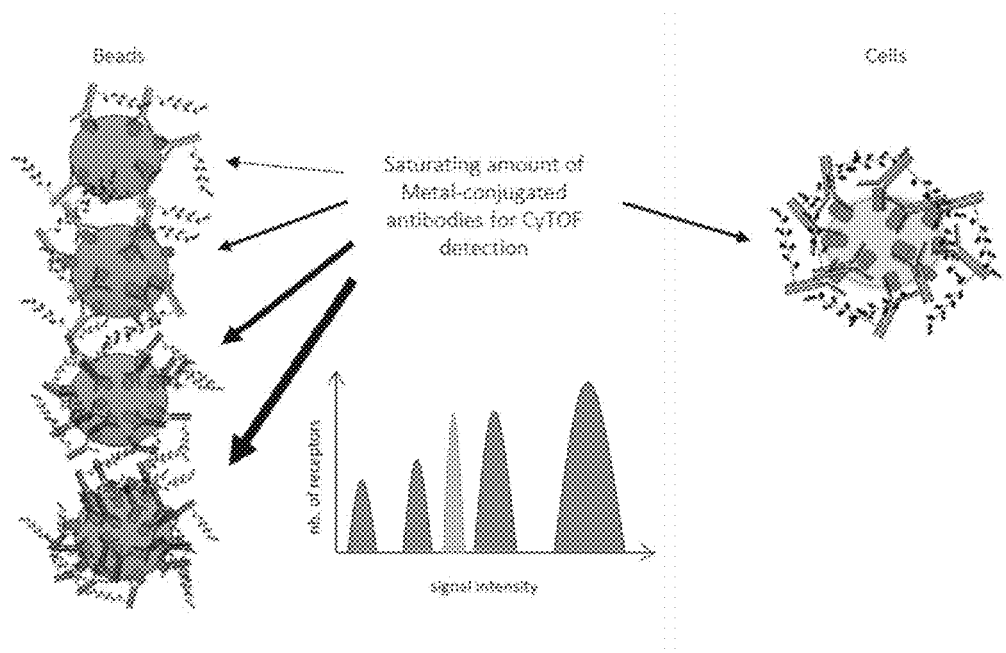
FIG. 8: Application of Osmium-labeled beads for absolute quantification of cell surface receptors. (a) Principle of application of Os-labeled beads for absolute quantification of cell surface receptors. Different concentrations of OsO4 are used to stain a set antibody capture beads with different Os intensities that are distinguishable by mass cytometry. The different beads preparations carry different, defined amounts of antibody capturing sites and were incubated with a CD4-144Nd antibody conjugate. (b) and (c) 5 Quantum™ Simply Cellular quantification carry different defined antibody capturing sites were incubated with an CD4-Nd144 antibody. (b) Dot plot showing all five Quantum™ Simply Cellular quantification bead populations labeled with different concentrations of OsO4 and their respective CD4-Nd144 signal (c) Histograms showing the separation of the 5 Quantum™ Simply Cellular quantification bead populations for their signals in the osmium and CD4-144Nd channel measured at CyTOF and for cross validation in the CD4-FITC channel at a conventional flow cytometer.
Figure 8:
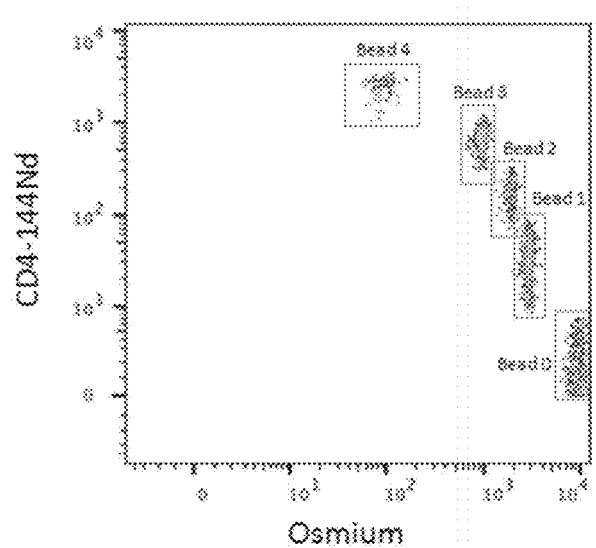
Figure 8:
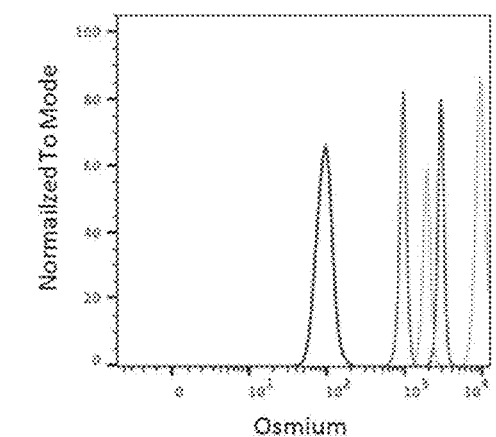
Figure 8:
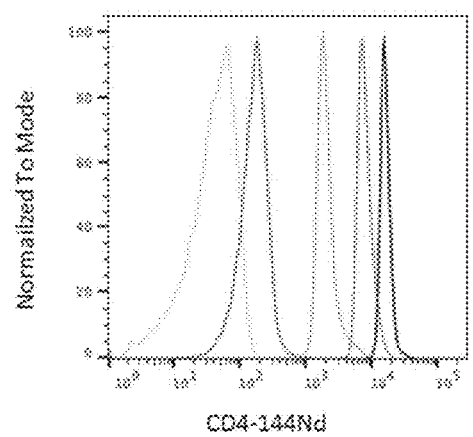
Figure 8:
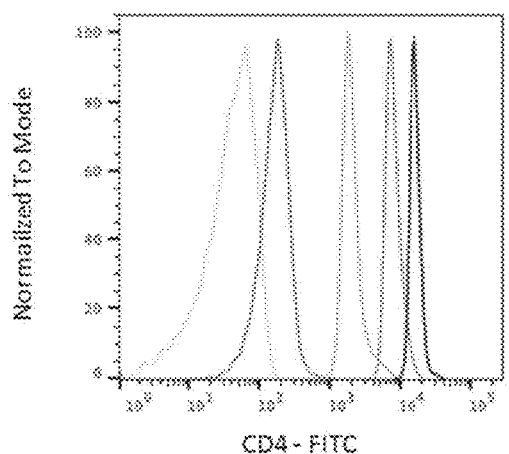

Equally sized aliquots of Os-stained antibody-capture beads loaded with individual antibody conjugates were pooled and used within hours or stored at −80° C. until use. Cells were stained with a cocktail of metal-labeled antibodies and further prepared as described for mass cytometry. Prior to sample acquisition, pooled beads and cells were mixed and analyzed together. Data of beads and cells were separated according to their Osmium and iridium signal intensity. Catalyst (Chevrier et al. 2018) was used for deconvolution of data from pooled beads, for calculating a spillover matrix and applying this matrix to the data of cells acquired along with the beads. FIG. 8 depicts sources of spillover in mass cytometry data, the workflow to generate compensation bead library, the distinction of cells and beads by Osmium and Iridium signals, and an example of a spillover matrix calculated from data of a bead library.

Ab Capture Beads for Absolute Receptor Quantification

Figure 12:
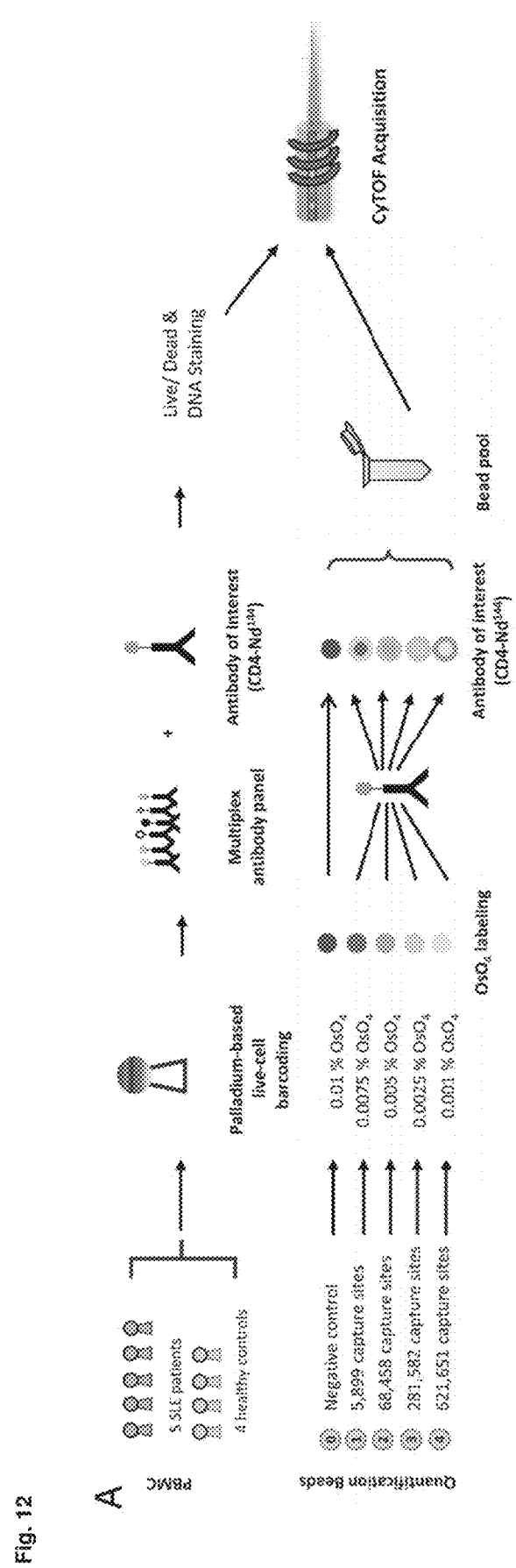
FIG. 12: Application of osmium-labeled beads for absolute quantification of four cell surface receptors in high-dimensional immune cell profiles of patients with SLE and healthy controls. (A) PBMC of five SLE patients, one IBM patient, and four age- and gender-matched normal controls were barcoded with a set of B2M Ab conjugates, pooled, and stained with a 42-parameter Ab panel, including CD4-114Nd (clone RPA-T4) for the determination of CD4 ABC, and acquired by the mass cytometer. Five different bead preparations with known ABC serving as reference were labeled with $OsO_4$ at gradually decreasing concentrations and incubated with the same CD4-144Nd Ab conjugate, pooled, and acquired by the mass cytometer. Reference data for Abs targeting HLA-DR, Siglec-1, and CCR6 were obtained in the same manner. The experiment was performed once. (B) Five reference bead populations were distinguishable according to their gradually increasing CD4-144Nd and decreasing osmium signals. (C) Comparison of ABC assay calibration data obtained by reference beads loaded with the same CD4 Ab clone (RPA-T4) in flow (black; Alexa Fluor 488) and mass cytometry (blue; 144Nd). Data in (B) and (C) are representative of at least four similar analysis. (D) Quantification of CD4, CCR6, HLA-DR, and Siglec-1 ABC in FlowSOM clusters of 42-dimensional mass cytometric immune profiles of five SLE patients and four controls prepared as described in (A). For each quantitated target, clusters exceeding the indicated ABC threshold are superimposed on a t-SNE projection of the entire dataset (upper row). (E) Scatter diagrams (lower row) show ABC values of the selected clusters of the individual SLE patients (red) and healthy controls (blue) and their group medians and interquartile ranges. Clusters with significantly different ABC values (p<0.05) between SLE patients and controls are indicated by an asterisk (Mann-Whitney U test). Color boxes match with cluster overlays in the respective t-SNE projections.
Figure 12:
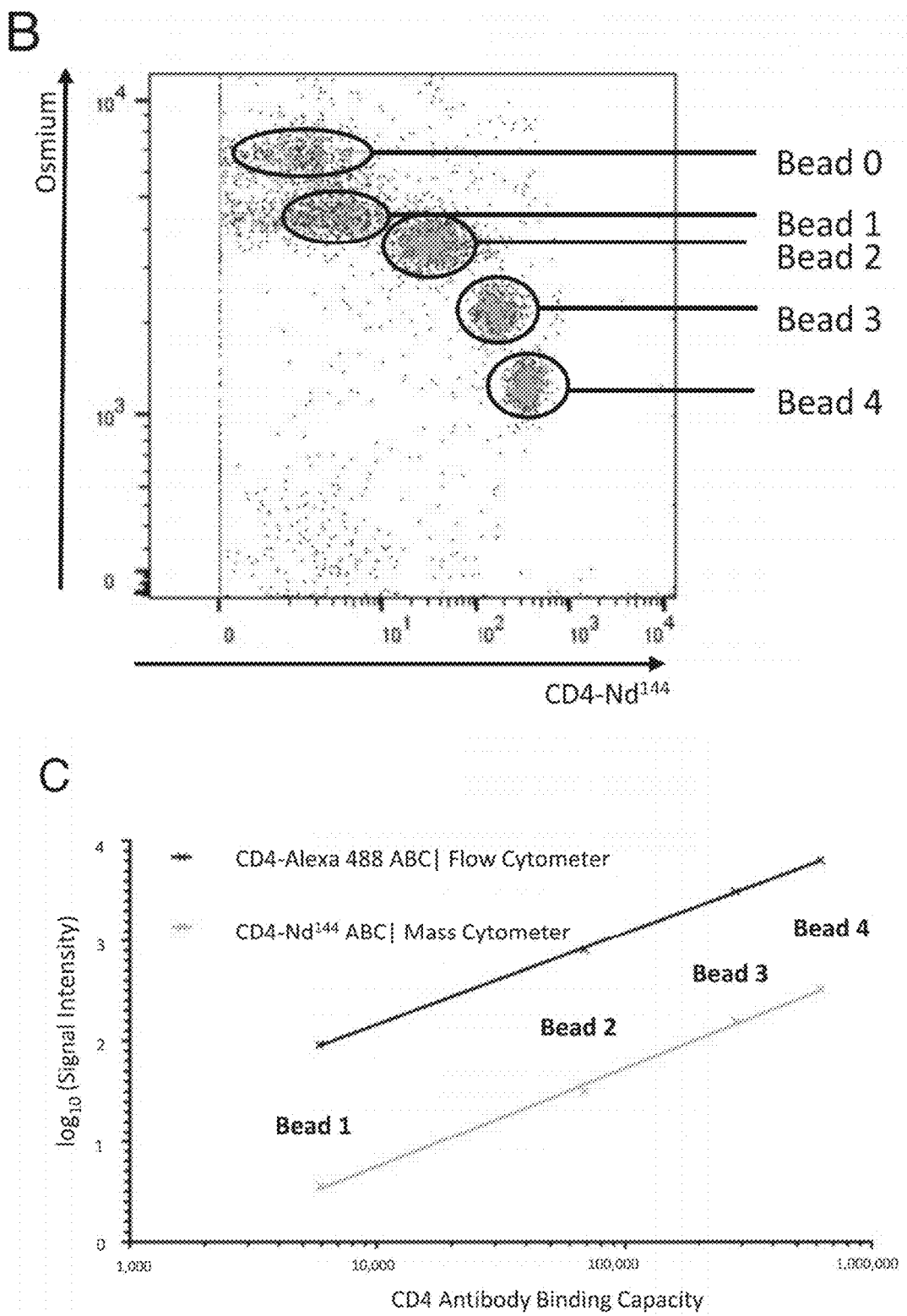
Figure 12:
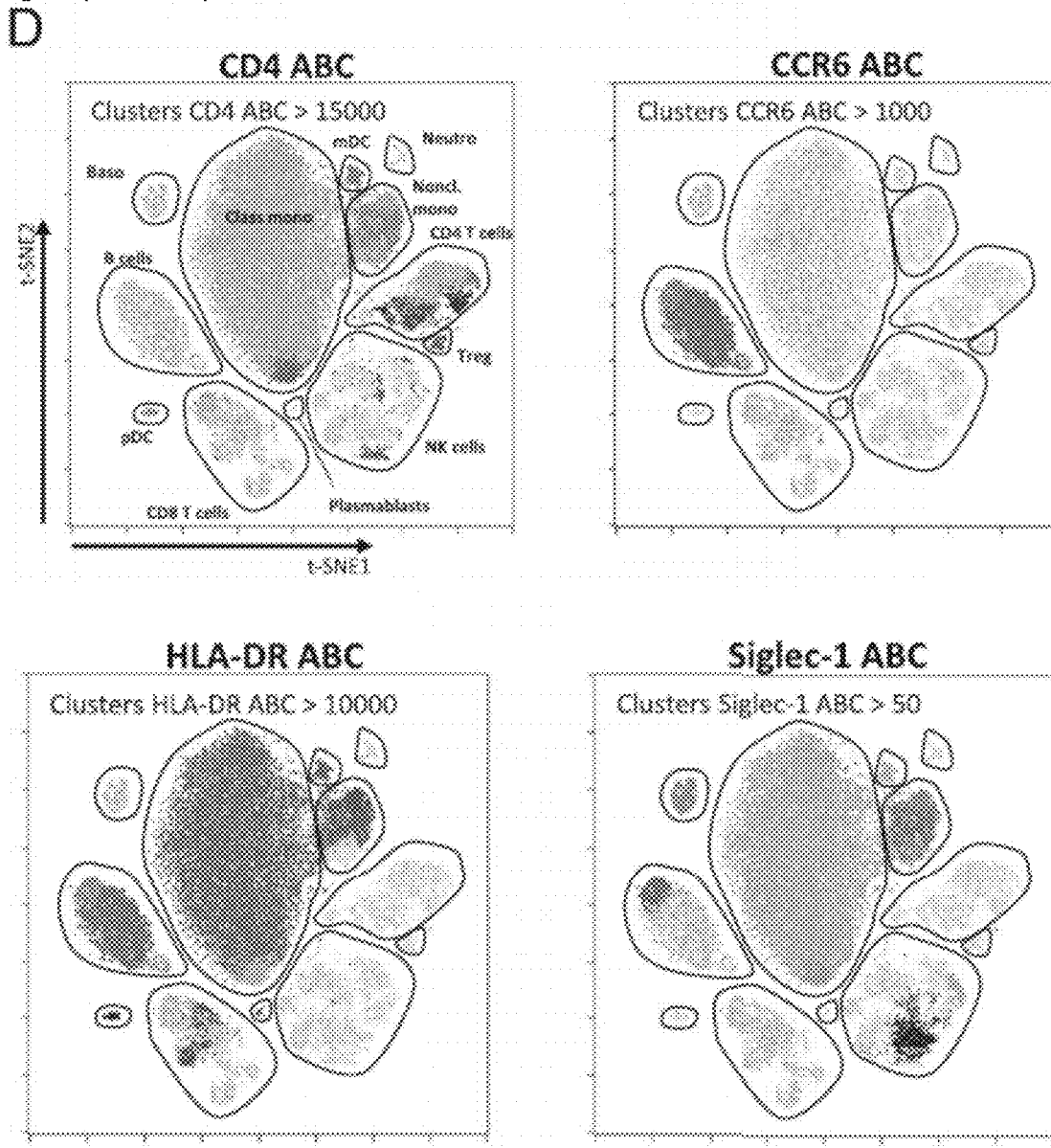
Figure 12:
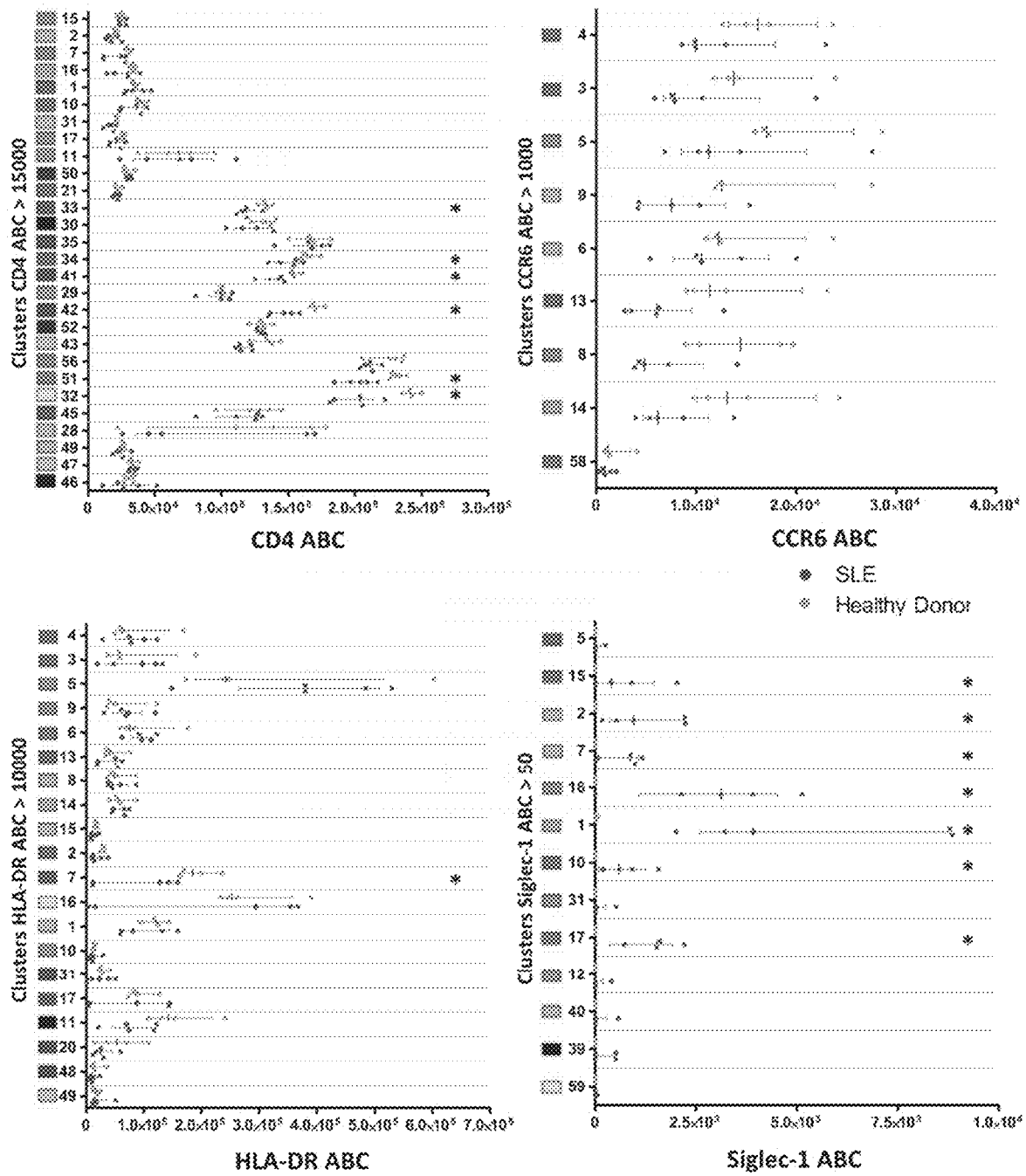

For absolute quantification experiments (ABC assays) shown in FIG. 12, QSC quantification beads (Bangs Laboratories, Fisher, Ind.) were implemented according to the manufacturer's instructions after labeling with $OsO_4$. To distinguish different bead population in mass cytometry data, $OsO_4$ labeling was performed with the following different concentrations of $OsO_4$ to achieve distinct osmium signal intensities: bead 0, 0.01% $OsO_4$; bead 1, 0.0075% $OsO_4$; bead 2, 0.005% $OsO_4$; bead 3, 0.0025% $OsO_4$; and bead 4, 0.001% $OsO_4$. After $OsO_4$ labeling, beads (except bead 0) were incubated with the Ab-metal conjugate targeting the cellular receptor of interest for 30 min at 4° C. The amount of applied Ab conjugate was determined by escalating the Ab conjugate concentration to achieve target saturation. For this, the concentration at which the maximum cytometric separation of stained bead 4 from unstained beads in the channel of interest, while not increasing background, was considered optimal and applied to beads 1-4 in the ABC assay. After incubation, the supernatant was removed by centrifugation (2500×g, 5 min). Different from Ab capture beads used for compensation, QSC beads were not exposed to PFA to mirror conditions applied to the beads in the flow cytometry-based ABC assays. QSC beads were always prepared freshly at the day of the experiment. For acquisition, the different bead populations were pooled and in some cases combined with PBMC and prepared for mass cytometric ABC assay (1:4, v/v). Beads for quantification experiments performed by flow cytometry were not labeled with $OsO_4$. The amount of Ab-fluorochrome conjugates necessary for saturation was determined in a similar manner as for mass cytometric quantification beads. The beads were processed according to the manufacturer's instructions and acquired on a MACSQuant flow cytometer (Miltenyi Biotec).

Data Analysis

Raw data were converted to FCS 3.0 files during acquisition. Data was normalized on the basis of EQ™ Calibration Bead signals using Fluidigm Helios software.

FCS files were analyzed using FlowJo (version 10.4, TreeStar, Ashland, Oreg.) and Cytobank Premium (www.cytobank.org). Statistical analyses were performed with GraphPad Prism (version 5.4, San Diego, Calif., USA). Calculation of signal spillover matrices and compensation was carried out with the R-package CATALYST (Chevrier et al., *Cell Systems* 6, 2018).

Results of the Examples

Osmium Labeling of Functionalized Beads

Figure 2:
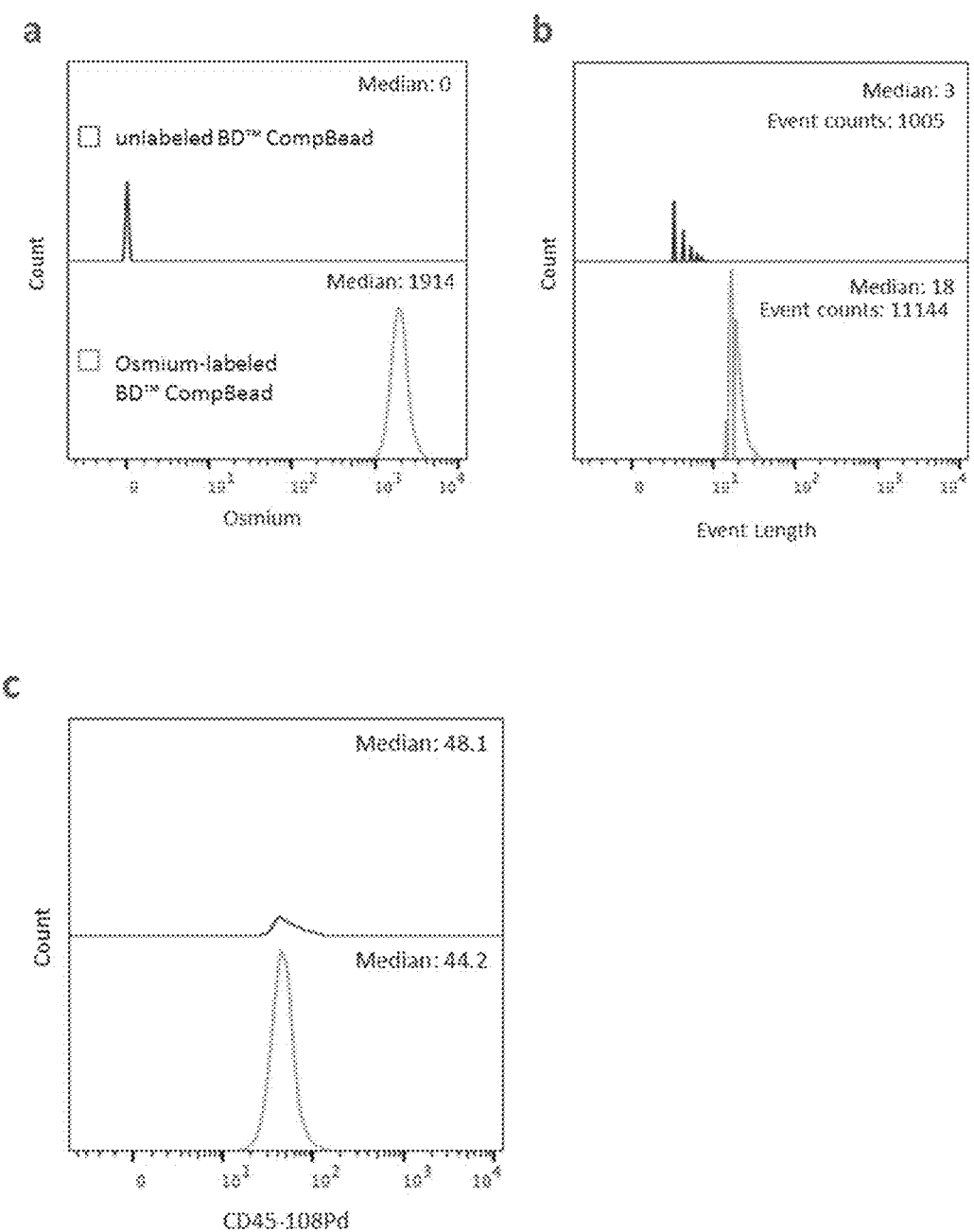
FIG. 2: Poor bead recovery on CyTOF instrument in the absence of Osmium staining. Comparison of event length and signal intensity (SI) for osmium-free (blue) or osmium-labeled (green) BD™ CompBeads capturing a CD45-Pd108 antibody conjugate. Data was acquired in two measurements with the same initial number of beads derived from one drop ($\sim 1*10^6$ beads). (a) Histogram of both bead population in the osmium channel. (b) Histogram of both bead preparations in the event length channel indicating the number of event counts and population distribution. (c) Histogram for signal intensities of both bead populations observed in the CD45-108Pd channel.

Osmium tetroxide has been used before to label cell membranes in electron microscopy and mass cytometry (Catena et al., *Cytometry* A. 89, 2016; Bozzola, J. J.; Russell, *Electron Microscopy: Principles and Techniques for Biologists*. 1999), as well as in material science to characterize carbohydrate based materials containing $C=C$ bond or aromate structures such as benzyl based compounds (Trent et al., *Polymer Science and Technology*, 1983). Here we use $OsO4$ to stain a variety of beads frequently employed in conventional fluorescence-based flow cytometry (FIG. 1), which often are made of polystyrene. The labeling was performed at low concentration of $OsO4$, under ambient conditions in PBS within 30 minutes. The resultant Os labeling of beads elicited a reproducibly high signal in mass cytometry (signal intensities usually >5.000), at intensities similar to the iridium signal resulting from treatment of cell with an iridium-containing DNA intercalator. Unlike beads not stained with $OsO4$, Os-labeled beads were quantitatively recovered in mass cytometric measurements, independent of the presence of, or signal intensity elicited by, a captured metal-antibody conjugate. Consistently, Os-labeled beads showed event length values (indicative of overall metal amount associated to a cell or bead event), with values routinely exceeding the standard lower threshold of 10, ensuring the proper detection by the mass cytometer and the event-detecting algorithm. Signals of the captured Ab conjugates showed the expected Gaussian distribution, also at low SI of approx. 5-50, that is, situations in which detection of beads lacking Os depends on the signal of the captured antibody is therefore unreliable in the absence of osmium staining (FIG. 2,3).

The results demonstrate Os labeling of beads for applications in mass cytometry. The staining is easy to perform, robust, and enables for the univocal detection of functionalized beads independent of their assay function by mass cytometry.

Robustness of the Protocol Against Changes in Staining Order, Storability of Os-Labeled Beads OsO4-labeled compensation beads could be univocally detected according to their corresponding signal in osmium isotope channels with more than 10% natural abundance (Os188, Os189, Os190, Os192) on the CyTOF instrument. The intensity of osmium labeling was well controllable by the OsO4 concentration in the staining solution, and concentrations between 0.001 wt.-% and 0.01 wt.-% OsO4 in PBS were identified as optimal to achieve sufficient Os staining intensity to exceed the lower event length cut-off (FIG. 4) and consistent labeling of beads across independent labeling procedures.

Figure 4:
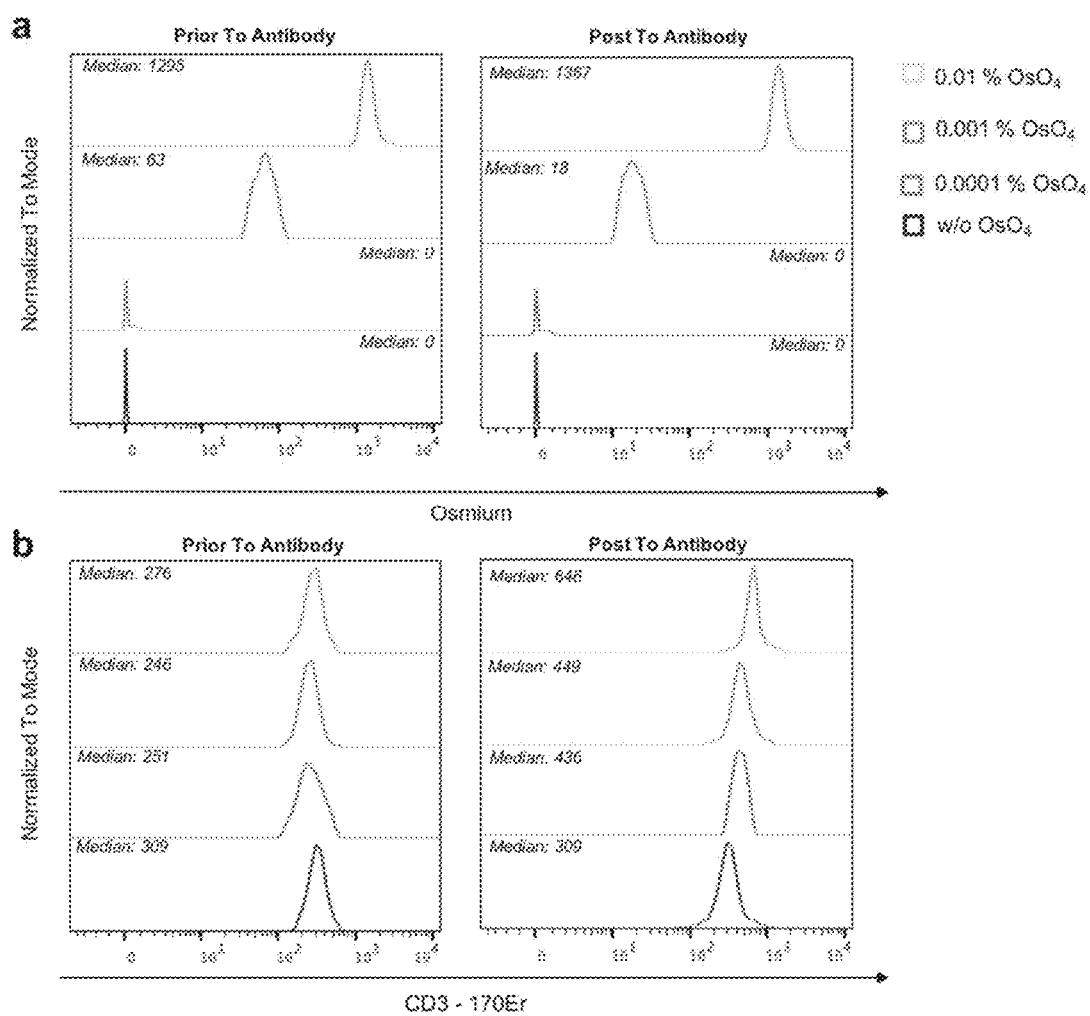
FIG. 4: Titration of optimal conditions for OsO4 labeling of the beads. Different osmium tetroxide concentrations were used to stain BD™ CompBeads before or after capturing CD3-170Er. (a) Osmium signal intensities of beads labeled with different osmium tetroxide staining solutions before (right) or after (left) antibody capture. Detection of osmium labeled beads is realized in the range of 0.001%-0.01% osmium tetroxide solutions. (b) Signal intensities of the captured antibody conjugate (CD3- 170Er) from the beads shown in (a)
Figure 5:
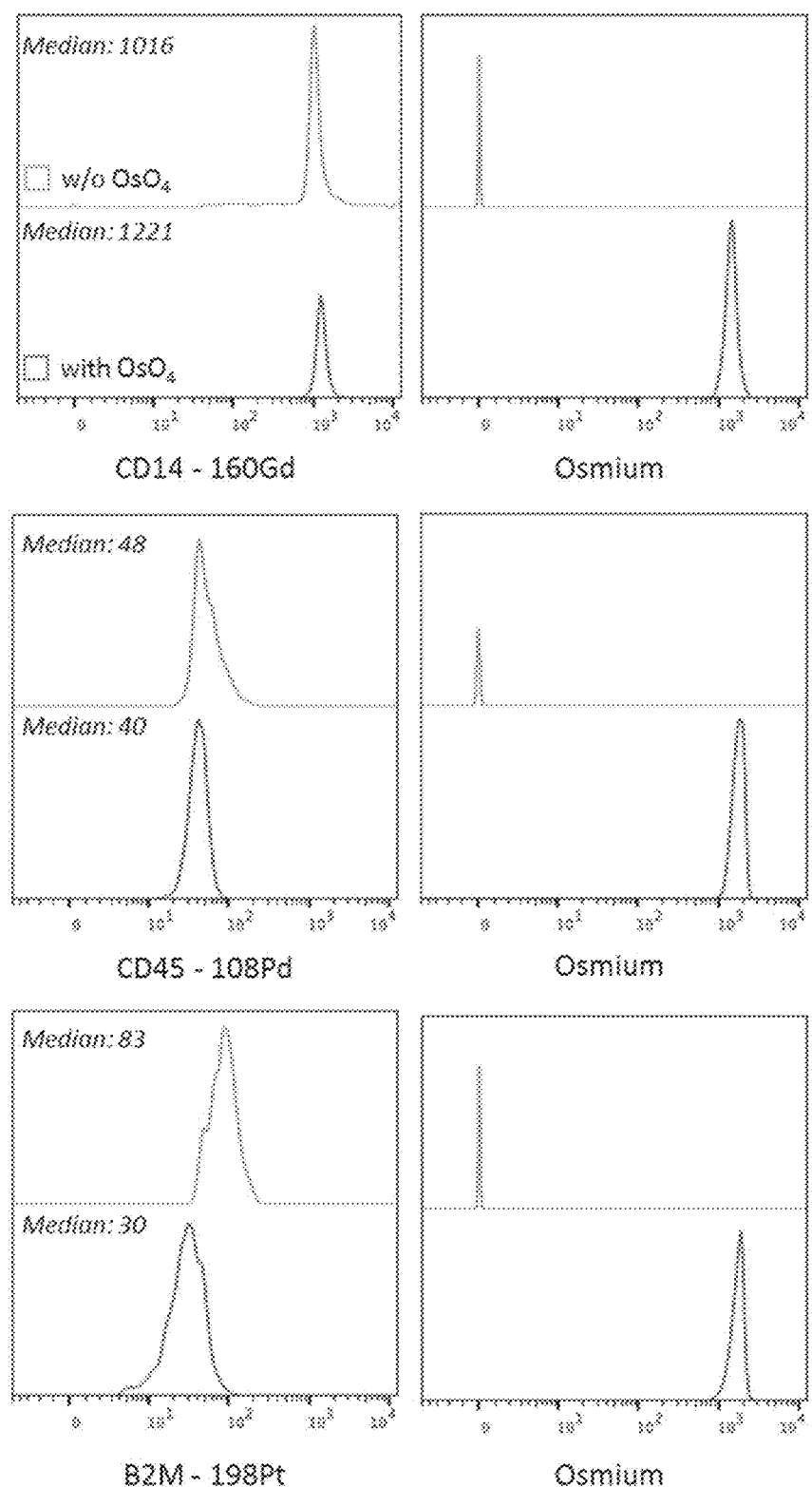
FIG. 5: Feasibility of osmium labeling for different common mass cytometry antibody conjugates. Validation of the feasibility of the osmium approach for palladium-, platinum- and lanthanide-conjugated antibodies on osmium labeled beads.
Figure 6:
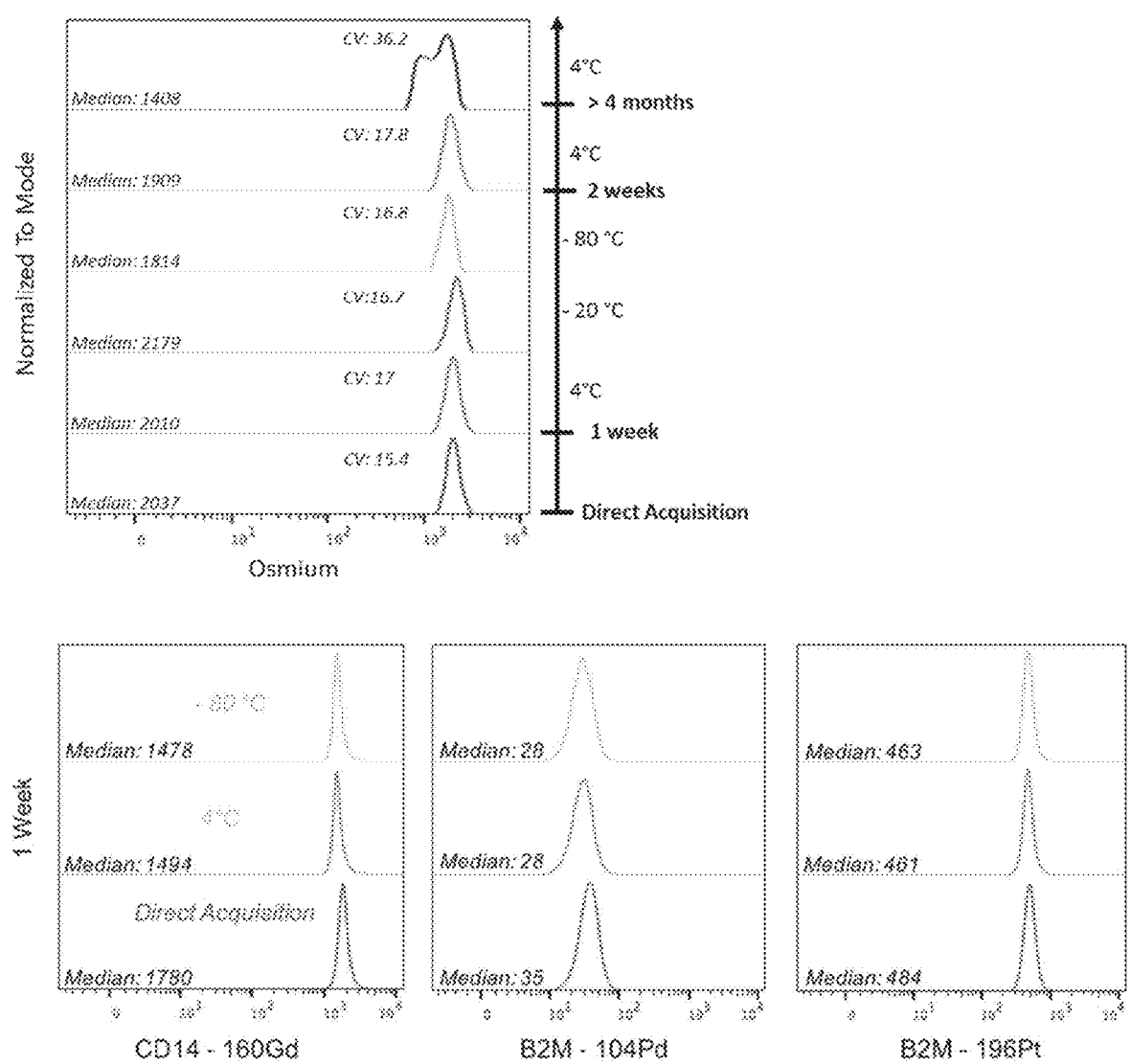
FIG. 6: Stable association of Osmium during long term storage of functionalized beads. Upper panel: Signal intensity of the osmium label for different storage conditions: Osmium-labeled antibody-capture beads can be stored in water for months at or below 4° C. with a marginal increase in the CV (coefficient of variation) over time. Lower panel: Signal intensities for a lanthanide-, palladium- and platinum-conjugated antibody captured by osmium labeled beads stored for 1 week at 4° C. and −80° C.

The influence of osmium tetroxide labeling on the functionality of antibody capture compounds immobilized on the bead surface was investigated. Metal-antibody conjugates were loaded onto commercially available antibody capture (BD) beads before or after bead labeling with OsO4 (FIG. 4). The results demonstrate that the capability of beads to capture antibody after OsO4 staining was preserved irrespective the OsO4 concentration of the staining solution. Likewise, OsO4 staining was successful when applied after the beads had captured metal-antibody conjugates. I summary, the effects of the order of osmium labeling and antibody capturing was absent or negligible on both, the Os signal and the capacity of the functionalized beads to bind antibody. This indicates that antibody proteins do commonly not contain structures bound by OsO4 so that both, capture antibody and the captured antibody can be considered intact.

As a result, the affinity-based binding between capture antibody and captured antibody remains undisturbed during OsO4 labeling. Once labeled with OsO4, the Os signal elicited by beads was stable for at least one week at room temperature or at 4° C. with marginal increase in the CV of Os signal (FIG. 4c), but no decrease of the median Os signal, so that longer-term storage of Os-labeled beads for flexible use in mass cytometry assays can be envisaged.

Versatility of the Os Staining Approach

Figure 7:
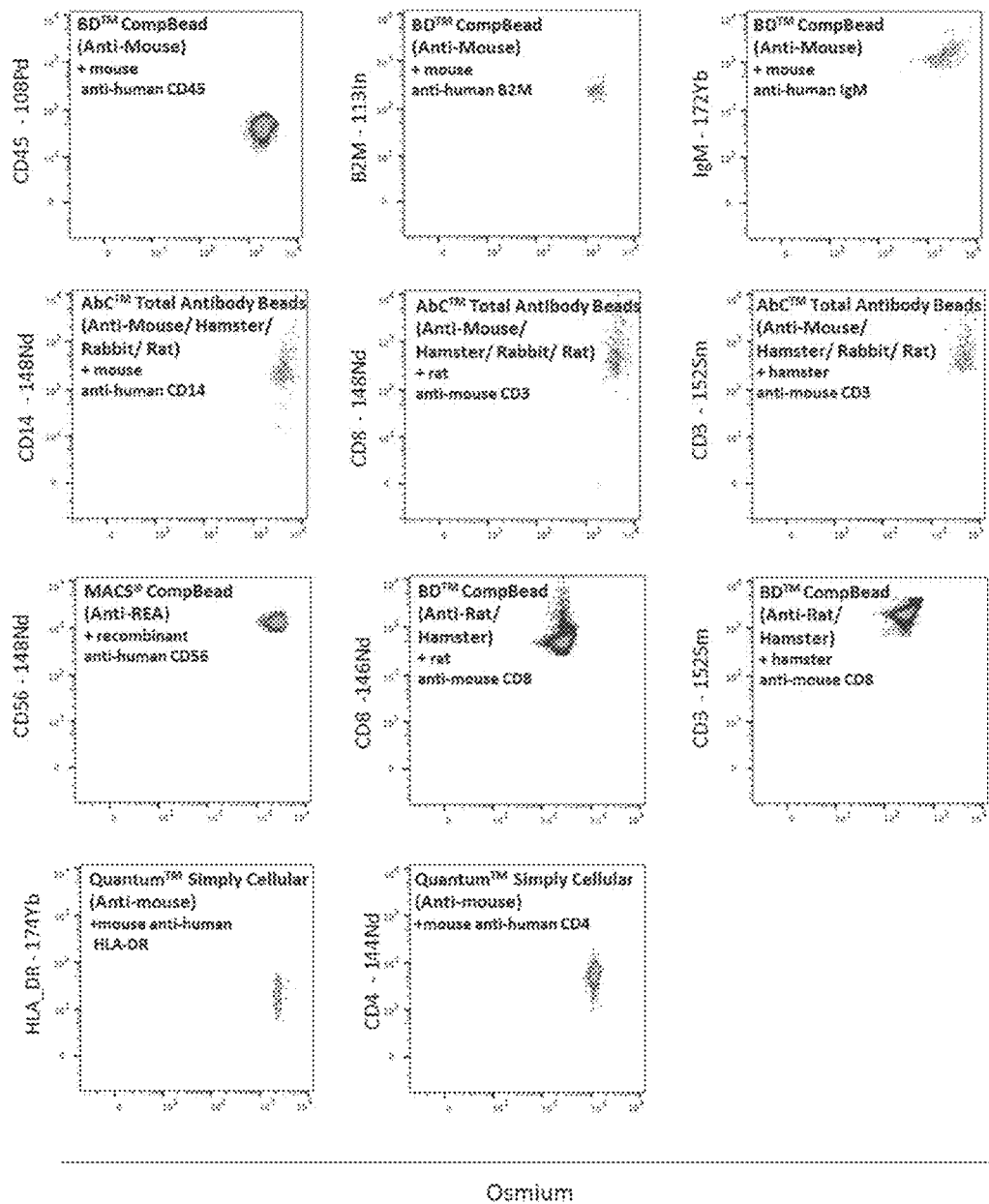
FIG. 7: Proof of versatility of staining approach: Functionalized beads from several vendors can be labeled with OsO4 and maintain their functionality. (a) Antibody capture beads from six different vendors were tested for their OsO4 labeling and maintained antibody capturing functionality. Tested beads included preparations that are designed to capture a large variety of analytical antibody expressed in mouse, rat, rabbit, hamster, rat, and recombinant chimeric REA antibodies and thus cover that vast majority antibodies used in cytometric assays. (b) Examples of beads tested and summarized in the table (a). Bivariate dot plots show Os signal vs the signal of the captured antibody.

Since antibody capture beads are an essential component in a recently published strategy to correct mass cytometry data for spillover arising from isotopic impurities and metal oxide formation (Chevrier et al., *Cell Systems* 6, 2018), we confirmed the utility of OsO4 staining for a series of commercially available beads that are tailored to capture a large variety of antibodies expressed in different species (mouse, rat, hamster, rabbit) or that have been engineered in humanized backbone (REA). As expected, all bead preparations tested were readily stained by OsO4 using the same protocol, with some variation in the resultant Os signal intensity (FIG. 7). However, Os staining was always sufficient to exceed the lower event length threshold of 10.

Figure 10A:
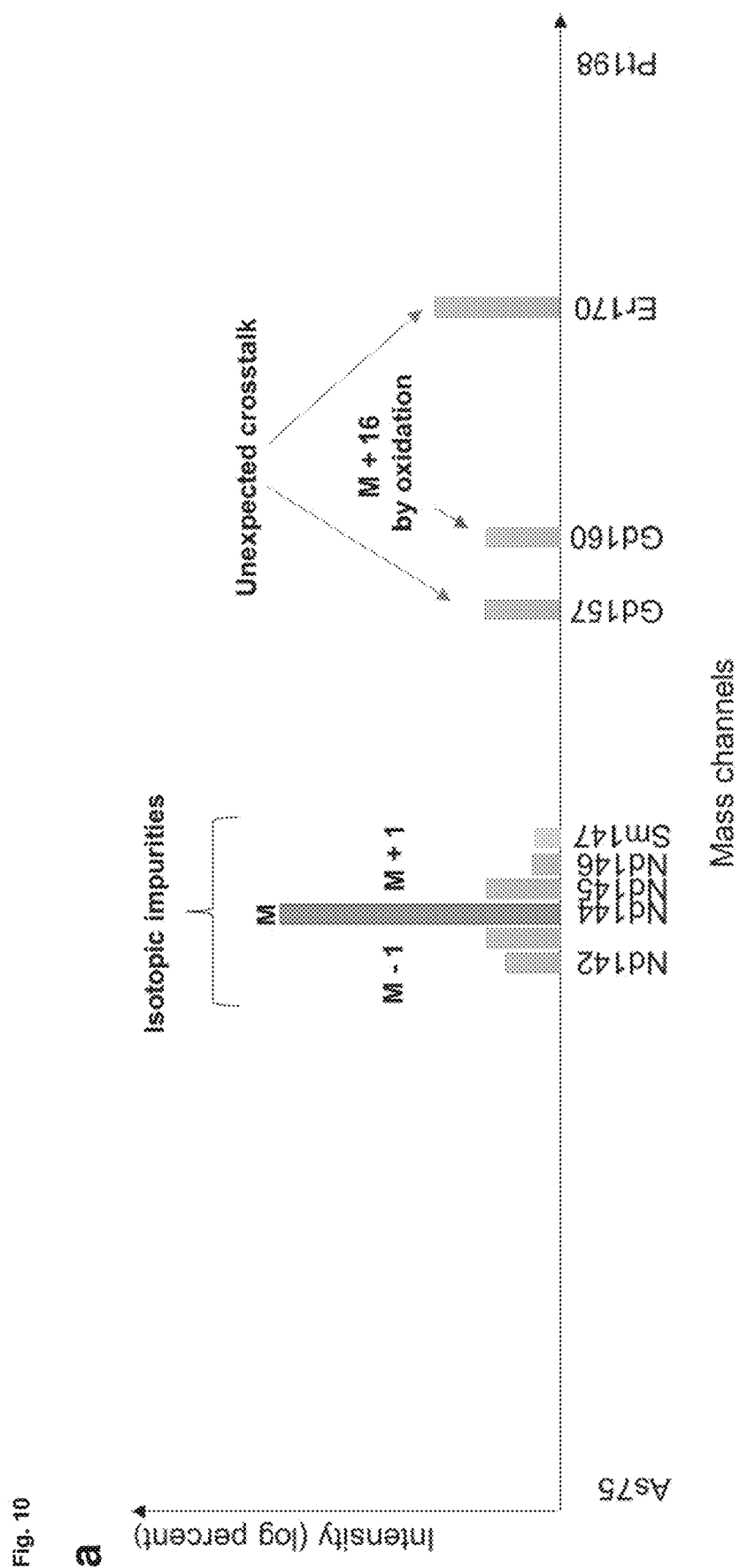
FIG. 10: Compensation of channel crosstalk in mass cytometry assays using Osmium-labeled beads stained with a representative library of metal-conjugated antibodies. (a) As depicted first, isotopic impurities, adjacent channel spill-over (M+1), crosstalk stemming from a metal oxidation (M+16) or unexpected crosstalk may lead to signal spill-over in undesired channels. (b) Second a schematic for a compensation strategy for channel crosstalk in mass cytometry assays using osmium-labeled beads is shown. Functionalized antibody-capture beads are labeled with osmium by incubating the beads with an osmium tetroxide solution as described herein. A representative library for different metal-conjugated antibodies is created by staining the osmium-labeled antibody-capture beads separately with the metal-conjugated antibodies that will also be used for parameterizing the cells. (c) Bivariate dot plot show Osmium signal vs the Iridium signal of osmium-labeled compensation beads and cells stained with an iridium-containing DNA-intercalating agent. Osmium-labeled compensation beads can be distinguished from cell events. (d) and (e) Compensation of beads representing a 44-plex panel. Osmium-labeled beads were single-labeled with anantibody conjugate of the respective panel and pooled before acquisition at CyTOF. t-SNE and dot plot projections of a mixture of single-stained, osmium-labeled compensation beads. Each cluster represents a different bead population capturing a specific antibody conjugate. 162Dy signals are shown for uncompensated and NNLS-compensated data (Bagwell et al., 1993; Chevrier et al., 2018), focusing on spill-over occurring due to isotopic impurity of the dysprosium isotopes and oxide formation of the 146 neodymium isotope. The osmium-labeled compensation beads allow for a quantification of spill-over occurring in the applied metal-conjugated antibody panel. (f) Spill-over matrix calculated from 25,000 beads of a 44-plex compensation bead library using the CATALYST algorithm (Chevrier et al., 2018). Beads were pre-gated for single bead events; the osmium signal was not considered for deconvolution. Spill-over was corrected by NNLS as indicated in (b) and (c) by the values of this matrix.
Figure 10:
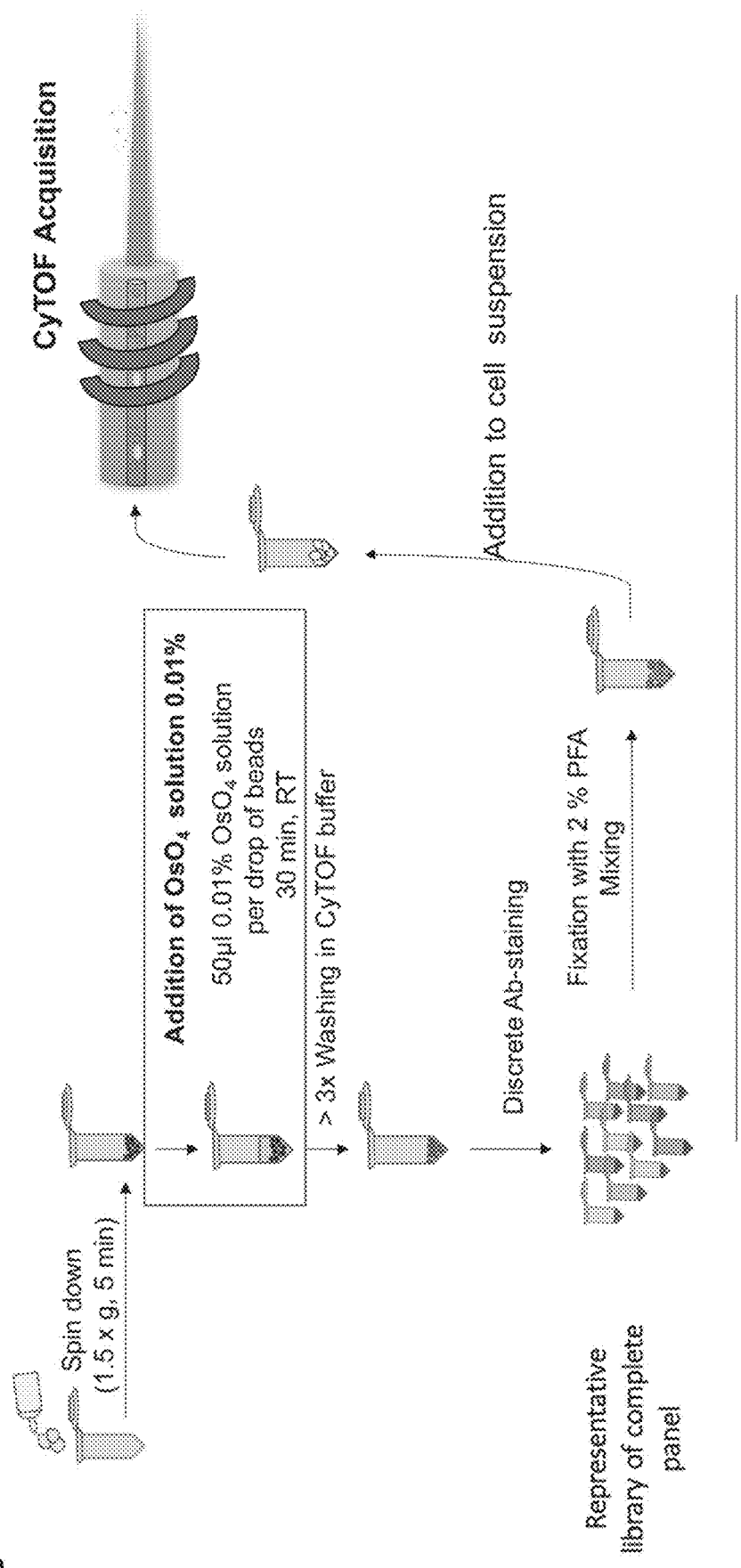
Figure 10:
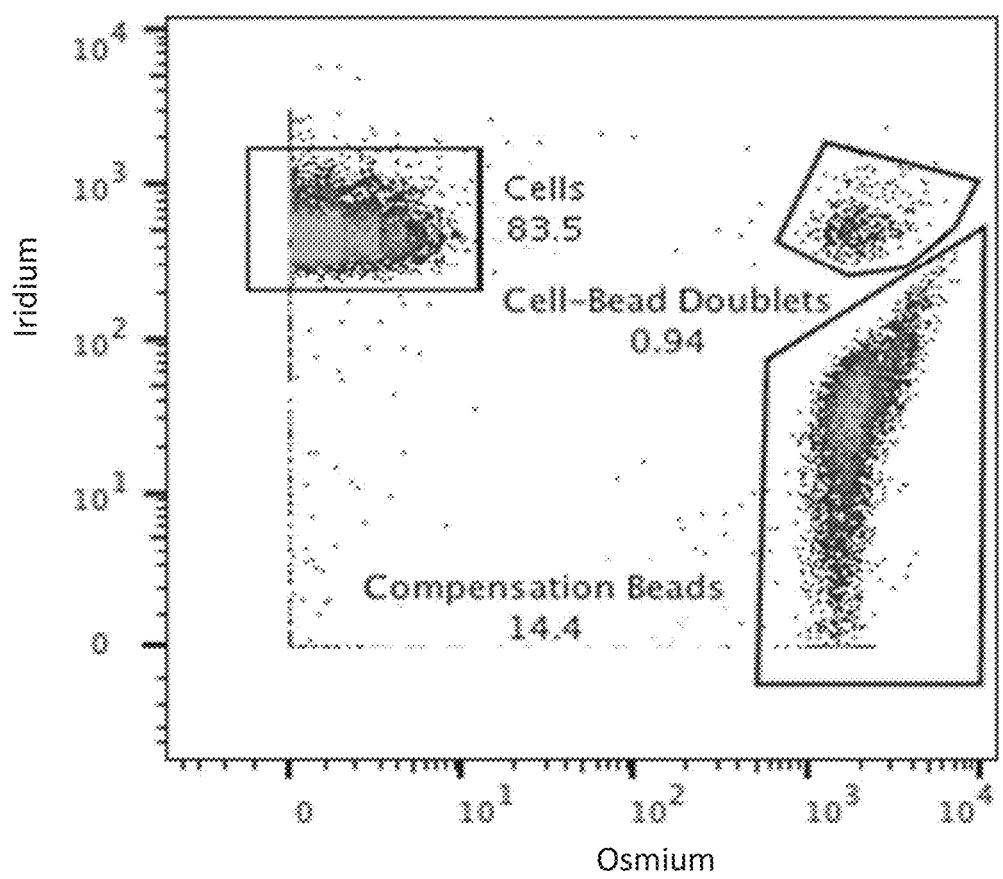
Figure 10:
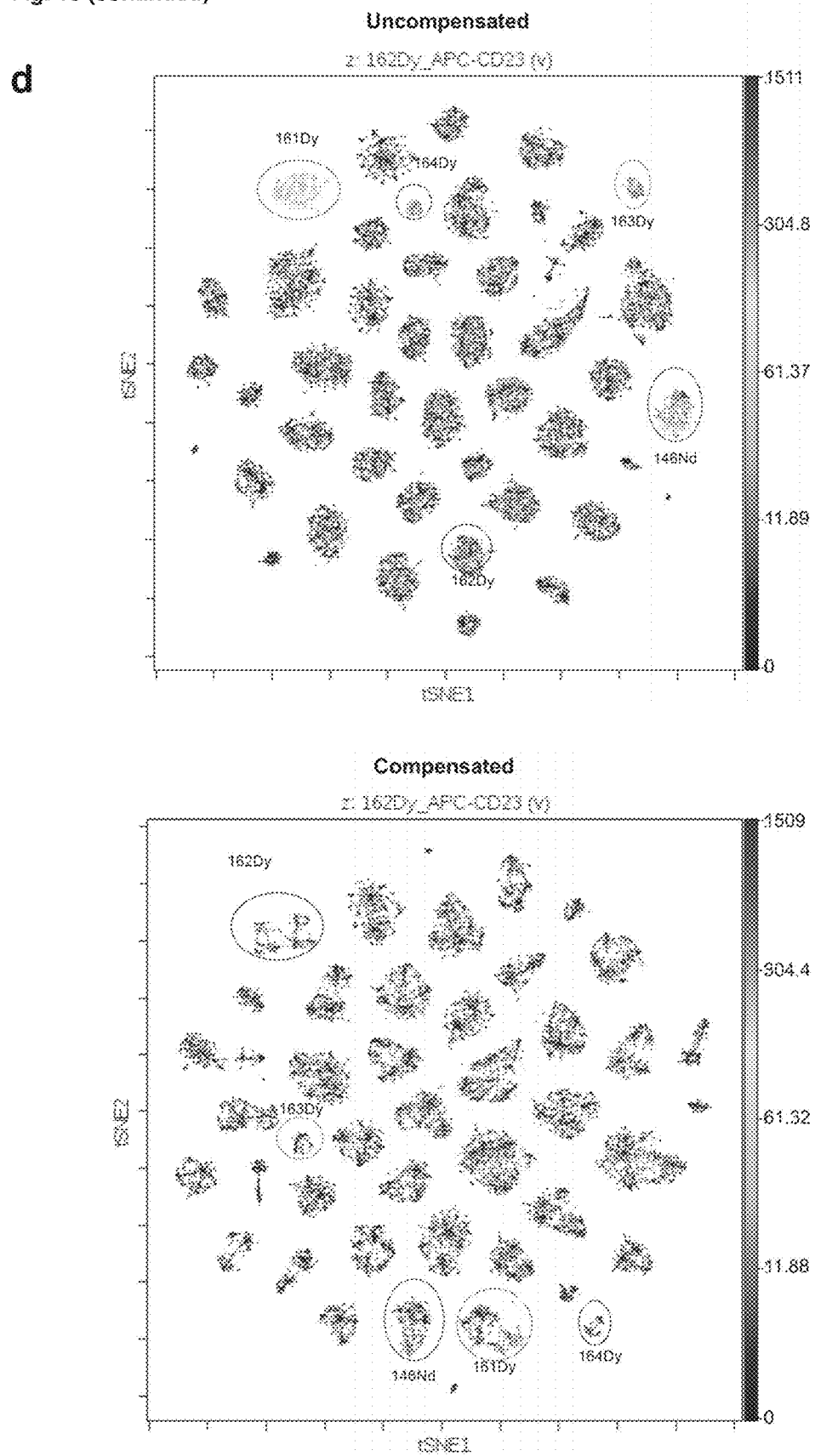
Figure 10:
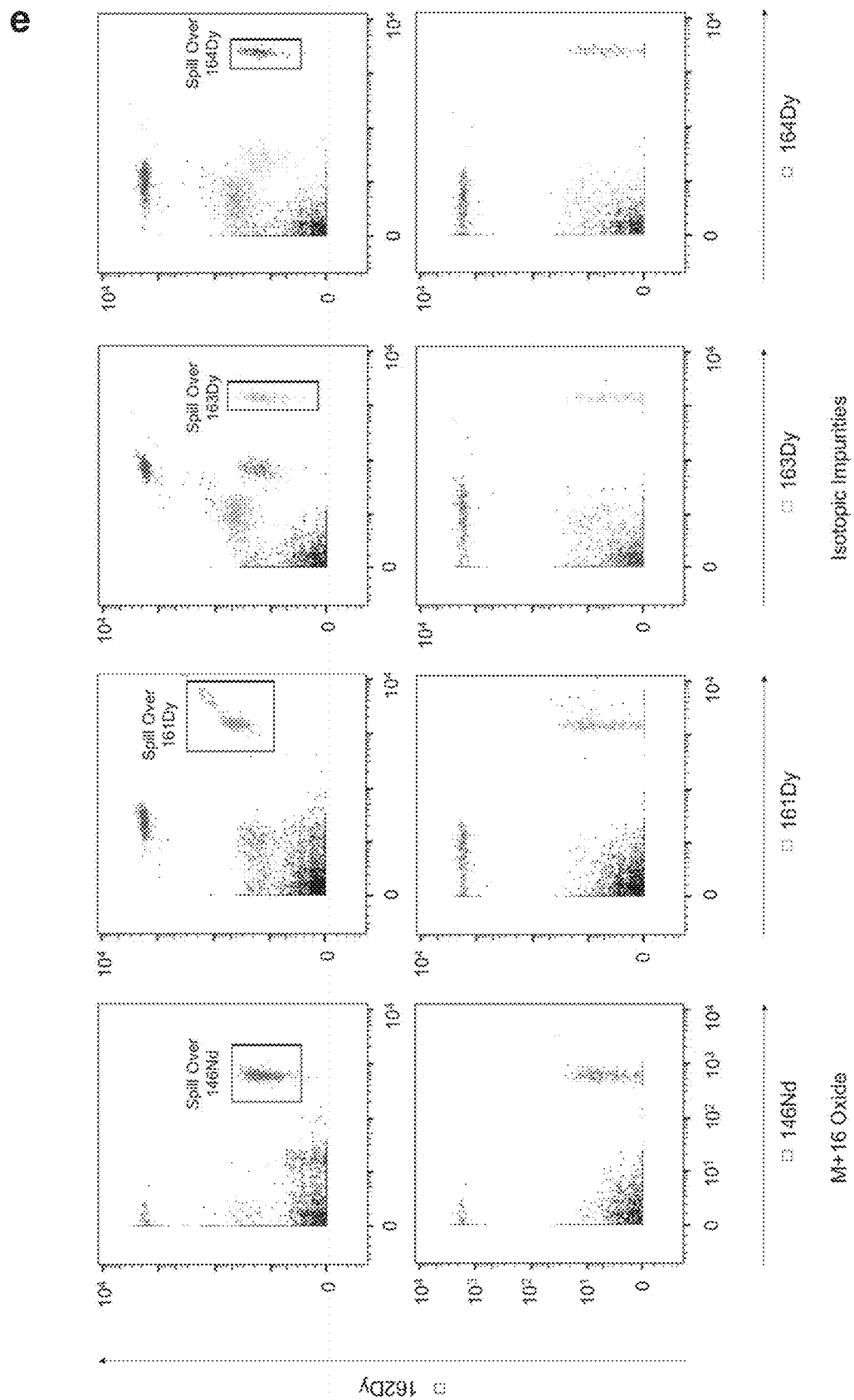
Figure 10:
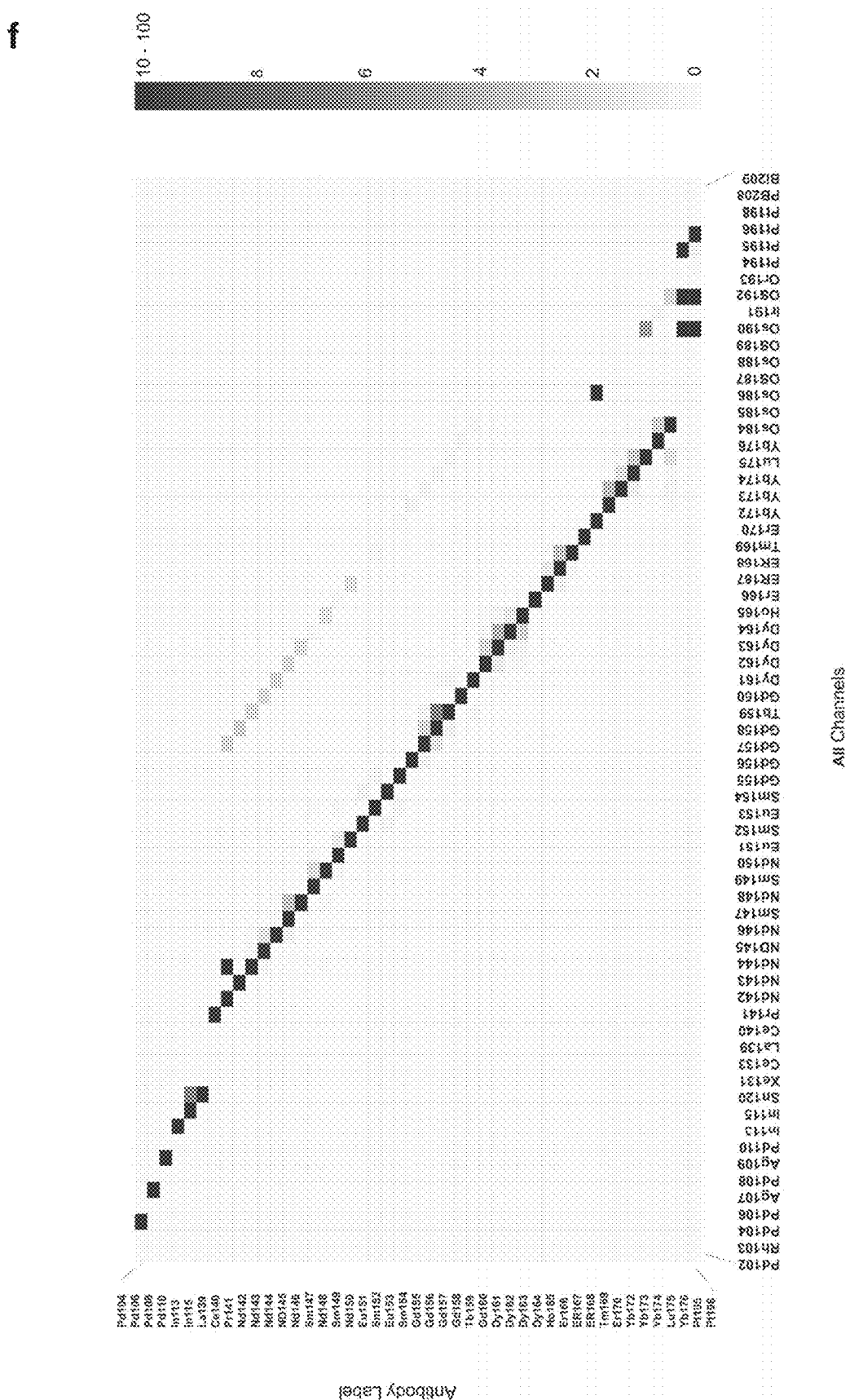

Application of Os-Labeled Beads in Time Resolved Compensation of Mass Cytometry Data A spillover compensation approach accounting for the signal spillover superimposed with signal drift effects in mass cytometry requires mixing compensation beads with its corresponding cell sample, and a specific label that allows to distinguish beads and cells in the data. We here use OsO4 staining of beads and DNA staining of nucleated cells to clearly distinguish bead and cell events based on osmium and Iridium signals (FIG. 10), and confirm that Osmium-labeled beads and iridium-labeled cells can be combined for acquisition on the CyTOF instrument without excessive carryover of signal or cell/bead doublet formation (FIG. 10).

FIG. 11 demonstrates further the potential of beads as described herein for the compensation for signal spillover between channels resulting from metal oxide formation and isotopic impurities of metal labels, which builds upon a recently proposed compensation strategy (Chevrier et al., *Cell Systems* 6, 2018).

In order to generate a spillover matrix Chevrier et al. stained aliquots of Ab capture beads (compensation beads) individually with a specific Ab conjugate from a mass cytometric Ab panel, pooled them, and acquired the bead convolute separately from cells. The approach is extended by using osmium-labeled Ab capture beads, which can be combined with the cell sample for joint acquisition (FIG. 11A). The osmium label discriminated the bead fraction from DNA intercalator-labeled cells, and all bead populations carrying individual Ab conjugates were detectable within the bead fraction (FIG. 11B). Catalyst (see Chevrier at al. et al., *Cell Systems* 6, 2018) was applied to bead data to calculate a spillover matrix, which was used to compensate spillover effects in bead and cell data.

For example, a representative Ab panel used CD20-$^{131}$In with an $^{113}$In purity of 93.1% beside CD3- $^{115}$In for detection of B and T cells, respectively. As expected, the majority of impurity in the $^{113}$In was explained by the presence of $^{115}$In, which resulted in an artefactual signal by B cells in the CD3- $^{115}$In detection channel (calculated spillover, 6.5%).

Figure 9:
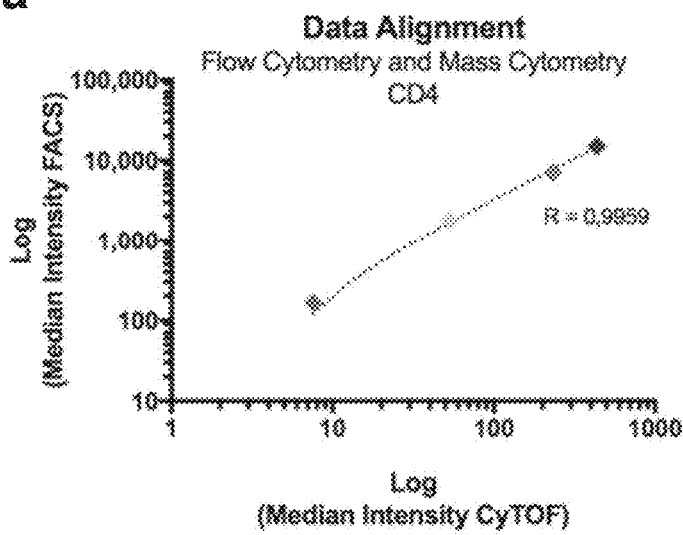
FIG. 9: Application of osmium-labeled Quantum™ Simply Cellular quantification beads for quantification of cell-surface expressed receptors in mass cytometry experiments. (a) Alignment of CyTOF and FACS data for each quantification bead stained with CD4-FITC (1:100 v/v, for all bead subsets) or CD4– 144Nd (1:25 v/v, for all bead subsets). (b) Dot plot of the quantification experiment (mass cytometry data) where beads and cells were combined for acquisition. The cell events are gated for single cell events representing CD3+CD14–CD4++ T-helper cells and CD3-CD14+CD4+ monocytes. The beads were gated according to their osmium and CD4-144Nd signal. X axis shows osmium staining. (c) Correlation of CD4-144Nd signal to receptor density of Quantum™ Simply Cellular quantification beads (1-4) and determination of cellular receptor density of the two cell populations (CD4++ T-helper cells, CD4+ monocytes) according to the cell related CD4-144Nd signal (median). (d) Box plot representing the interpolated different CD4-144Nd antibody binding capacities (ABC) of T-helper cells and CD4-positive monocytes from the investigated population.
Figure 9:
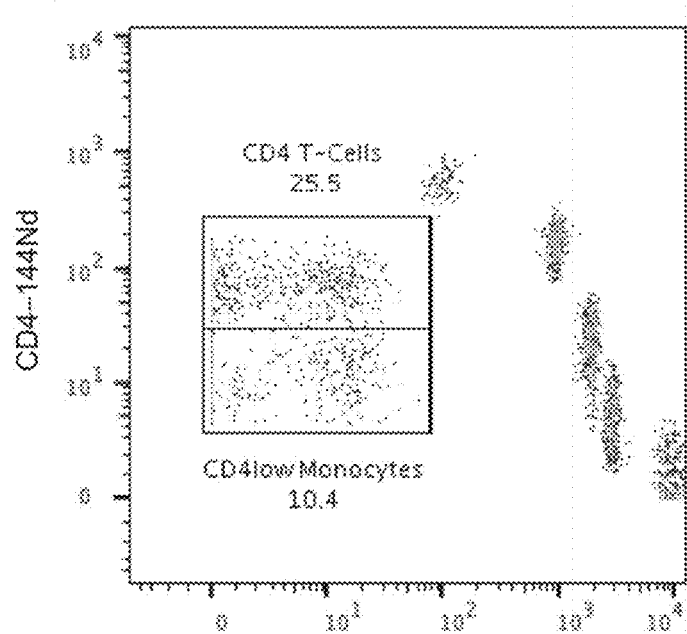
Figure 9:
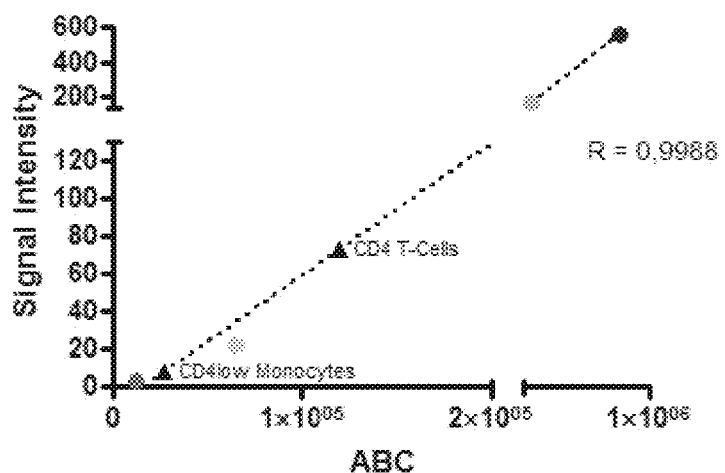
Figure 9:
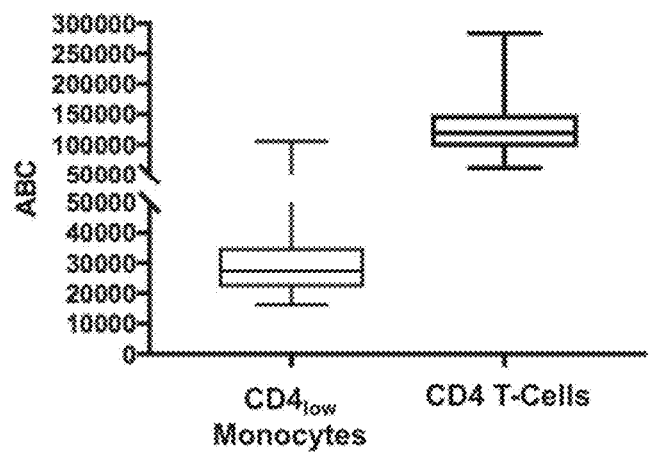

Compensation using osmium-labeled beads and Catalyst properly corrected the spillover artifact, thereby improving data accuracy and facilitating proper interpretation (FIG. 11C, 11D). Notably, once prepared, compensation bead pools were storable at −80° C. for at least 2 wk without affecting the signal intensity of the capture Ab conjugates, simplifying its use as a routine spike-in compensation control in mass cytometry Application of Os-Labeled Beads in Quantification of Cellular Receptor Density Beads equipped with different, known number of antibody capturing sites are used in flow cytometry to generate a reference curve for determining the number of receptors recognized by a fluorescently labeled Ab. Here we use Os-labeling of beads to transfer this assay to mass cytometry for its application in high-dimensional data. The reference consists of a set of 5 different bead population that were stained with different concentration of OsO4 to achieve different Os Signal intensity levels that makes the bead populations distinguishable in mass cytometry data. All beads subsets capture the amount of (CD4-Nd144) antibody under saturating conditions, so that the number of Ab binding sites on each bead subsets determines (limits) the SI of Nd144 (FIG. 8). This data serves as reference for calculating the number of CD4 molecules on cell subsets contained in PBMC. We show that the reference values obtained from Quantum™ Simply Cellular quantification beads loaded with CD4 antibody conjugates by flow and mass cytometry correlate very well (FIG. 9a), and that cells and beads can be pooled for acquisition (FIG. 9b), enabling the recording of reference beads along with the cells of interest, providing ideal conditions for the technical consistency between cell sample and reference beads. CD4 signal intensities of CD4++ T cells and CD4+ monocytes (known to express lower levels of CD4 compared to CD4++ T cells) were determined and plotted into the graph showing bead-based reference data (FIG. 9c,d).

FIG. 12 further exemplifies the utility of osmium-labeled beads for combining cell surface receptor quantification assays with high dimensional immune cell phenotyping by mass cytometry by analyzing five SLE-active patients and four control donors using 42-dimensional mass cytometry.

After analyzing the abundance of FlowSOM clusters in SLE versus control PBMC, revealing multiple aberrations, including reduced frequencies of CD8+ T cell, CD4+ T cell and B cell clusters, and increased frequencies of a monocyte cluster consistent with known lymphopenia in SLE, the same data was used to analyze the expression of four different receptors (CD4, HLA-DR, Siglec-1, and CCR6) at the level of absolute ABC quantification across all clusters in high-dimensional phenotypic space. For each target, one set of QSC beads equipped with known, gradually increasing numbers of Ab-binding sites were labeled with OsO$_4$, incubated with the Ab conjugate, pooled, and acquired directly before acquisition of the cell sample by the mass cytometer. Bead data served as reference for the determination of ABC (FIG. 12A, 12B).

Notably, calibration curves exhibited very similar slopes for the CD4 and HLA-DR assays that were performed by both flow and mass cytometry (flow cytometry: 0.9168; mass cytometry: 0.9817, FIG. 12C). This demonstrates that despite employing biophysically fundamentally different detection methods, the assay calibration worked comparably well in flow and mass cytometry.

In addition, mass cytometric ABC assays were reliably reproducible, confirming the robustness of the approach. Because CD4 ABC have been quantified in various studies before, CD4 ABC in select PBMC subsets of our data were first analyzed to enable a direct comparison with previous data. A median of 140,677 CD4 Abs per cell on Th cells (minimum: 126,861; maximum: 160,378 Abs per cell; 10 donors) was determined.

As expected, the CD4 ABC of monocyte subsets and pDC was much lower than that of Th cells (median: 20,367-44,886 Abs per cell, FIG. 12A). Because those data were largely consistent with other studies, providing confidence in the approach, a systematic comparison of CD4, HLA-DR, Siglec-1, and CCR6 ABC across all PBMC subsets derived from FlowSOM clustering between five SLE patients and four healthy controls was performed.

Despite the few individuals analyzed, this analysis revealed several distinct clusters with significantly reduced CD4 or HLA-DR ABC or enhanced Siglec-1 ABC in patients with SLE. CCR6 ABC showed high interindividual variation and were not found significantly dysregulated in SLE (FIG. 12D). HLA-DR ABC were found diminished in cluster 7, showing the phenotype of myeloid dendritic cells (mDC) (high expression of CD36, CD11c, and CD1c; low or no expression of CD3, CD19, CD56, CD16, and CD14), and the increase of Siglec-1 ABC was documented in seven clusters with dominant monocyte or mDC features.

Because all clusters with reduced CD4 ABC were Th cells, manual gating and CD4 ABC analysis of CD4+ T cells and their major subsets were exemplarily performed, confirming the result of the systematic analysis (reduction of CD4 ABC by 14%, p=0.0156). Interestingly, low HLA-DR ABC on mDC were strongly associated with low CD4 ABC of certain Th cell clusters.

Combining unsupervised clustering of high-dimensional mass cytometry data with receptor expression level analysis sensitively identified known and novel immune cell aberrations in active SLE, illustrating the utility of bead-based assays in biomarker identification studies. Osmium-labeled beads thus facilitated the integration of ABC assays in high-dimensional immune phenotyping studies by mass cytometry, extending its application range.

What is claimed is:

1. Method of analyzing beads as control, calibration and/or quantification probes in a mass cytometry assay, comprising the steps of
   a. providing a mass cytometer
   b. providing cells to be probed in said mass cytometer
   c. providing beads, the beads are labeled with a heavy metal selected from the group consisting of osmium and ruthenium, wherein the beads are synthetic polymeric beads and have been labelled with osmium by incubating the beads with an osmium tetroxide dilution or have been labeled with ruthenium by incubation the beads with a ruthenium tetroxide dilution,
   d. performing a mass cytometry assay including the steps of incubating the cells with one or more mass tagged affinity reagents, wherein the one or more mass tagged affinity reagents are metal conjugated antibodies configured for a specific binding to cellular target molecules of said cells such that a quantity of mass tagged affinity reagents allows for a determination of the presence of the cellular target molecules on said cells, and conducting an elemental analysis of said cells and beads using the mass cytometer,
   wherein said beads are analyzed as a control, calibration and/or quantification probe in said mass cytometry assay.

2. The method according claim 1, wherein the beads exhibit a surface functionalization allowing for the binding of the one or more mass tagged affinity reagents to the surface functionalization of said beads.

3. The method according to claim 2, wherein the one or more affinity reagents allowing for the binding to the surface functionalization of the beads is/are an antibody and the surface functionalization refers to the presence of antibody capturing sites.

4. The method according to claim 1, wherein the beads are polystyrene beads.

5. The method according to claim 1, wherein the beads have a size of 10 nm to 100 μm.

6. The method according to claim 1, wherein the concentration of the heavy metal tetroxide diluted in the buffer solution is in between 0.0001 wt.-% to 0.01 wt.-%.

7. The method to claim 1, wherein the beads exhibit a surface functionalization allowing for the binding of an affinity reagent to the surface functionalization of said beads and that the step of providing the beads includes a step of providing beads labeled with the affinity reagent and/or the method further includes a step of labelling the beads with the affinity reagent and wherein the affinity reagent is preferably an antibody, most preferably a metal-conjugated antibody.

8. The method according to claim 1 wherein:
   the beads are provided in one or more groups of the beads labeled with the heavy metal, and
   the mass cytometry assay is performed by introducing said beads and said cells into the mass cytometer for the elemental analysis, wherein data acquired from said beads is used for the compensation of the channel-cross talk or the spill-over in the data acquired from said cells.

9. The method according to claim 1 wherein:
   the beads are provided in at least two groups of the beads labeled with the heavy metal and exhibiting the surface functionalization allowing for the binding of the one or more mass tagged affinity reagents to the surface functionalization of the beads, wherein
   the beads of each of the at least two groups exhibit as the surface functionalization a different defined amount of antibody capturing sites and are labeled with a different defined amount of osmium or ruthenium,
   the one or more mass tagged affinity reagents are one or more metal-conjugated antibody/antibodies targeting a cell surface receptor or cell surface receptors,
   the least two groups of beads are incubated with the one or more metal-conjugated antibody/antibodies under saturating conditions,
   the mass cytometry assay is performed by introducing a mixture of said beads and said cells into the mass cytometer for the elemental analysis, and
   wherein said method further comprises:
   calculating a reference curve from the data acquired from the at least two groups of beads yielding a correlation between signal intensity detected in the mass cytometer and absolute amount of metal-conjugated antibodies, and
   using said reference curve for an absolute quantification of cell surface receptors,
   wherein the method is used for an absolute quantification of cell surface receptors in the mass cytometry assay.

* * * * *

UNITED STATES PATENT AND TRADEMARK OFFICE
CERTIFICATE OF CORRECTION

PATENT NO. : 11,307,206 B2
APPLICATION NO. : 16/395022
DATED : April 19, 2022
INVENTOR(S) : Henrik Mei It is certified that error appears in the above-identified patent and that said Letters Patent is hereby corrected as shown below:

In the Specification

Figure 3:
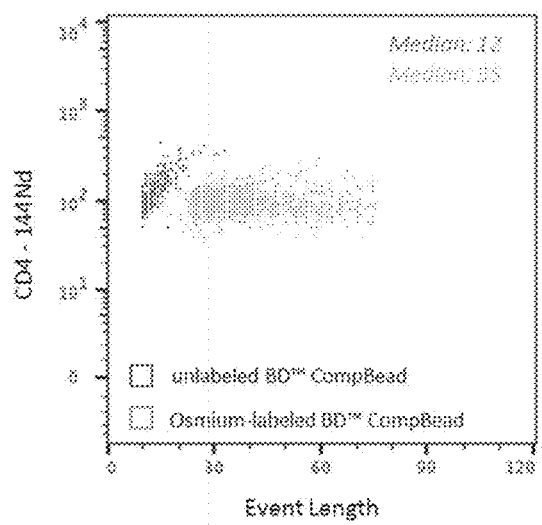
FIG. 3: Compromised readout signal from antibody capture beads in the absence of Osmium staining. Comparison of event length and signal intensity (SI) for BD™ CompBeads capturing a CD4-144Nd antibody conjugate when stained with osmium tetroxide (green) or not (blue). The same number of beads ($1 \times 10^6$) was used for all assays. (a) Event length for each bead population observed in the CD4-144Nd channel (bivariate dot plot). (b) Histogram of bead populations for the respective event length of beads (event length threshold: 10). (c) Histogram of both bead population for the respective signal intensities in the osmium channel. (d) Histogram of both bead populations for the CD4-144Nd signal intensity with the incidental statistical values for median and CV (coefficient of variation).
Figure 3:
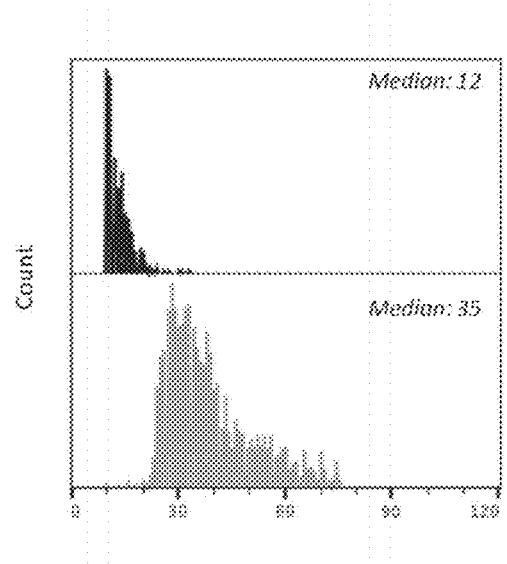
Figure 3:
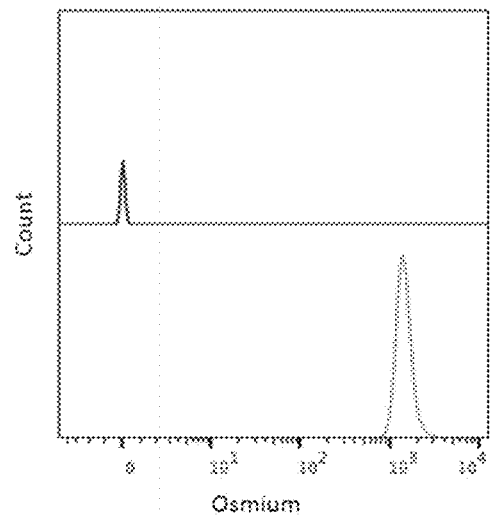
Figure 3:
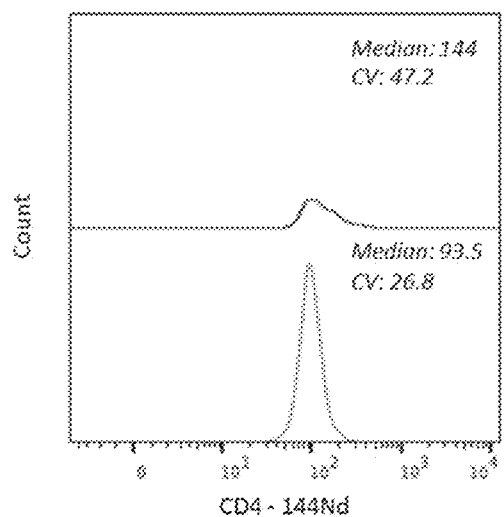

Column 1, Line 3, below "CYTOMETRY" insert -- DESCRIPTION --.
Column 2, Line 33, delete "enyzme-linked" and insert -- enzyme-linked --.
Column 10, Line 49, delete "analysis," and insert -- analysis. --.
Column 14, Line 42, delete "(CD3- 170Er)" and insert -- (CD3-170Er) --.
Column 14, Line 43, delete "(a)" and insert -- (a). --.
Column 15, Line 64, delete "anantibody" and insert -- an antibody --.
Column 16, Line 45, delete "CD3- $^{115}$In." and insert -- CD3-$^{115}$In. --.
Column 17, Line 35, delete "$^{85}$Os," and insert -- $^{185}$Os, --.
Column 24, Line 12, delete "(FIG. 2,3)." and insert -- (FIGS. 2, 3). --.
Column 25, Line 36, delete "CD20-$^{131}$In" and insert -- CD20-$^{113}$In --.
Column 25, Line 37, delete "CD3- $^{115}$In" and insert -- CD3-$^{115}$In --.
Column 25, Line 41, delete "CD3- $^{115}$In" and insert -- CD3-$^{115}$In --.
Column 25, Line 45, delete "(FIG." and insert -- (FIGS. --.
Column 25, Line 50, delete "cytometry" and insert -- cytometry. --.
Column 26, Line 12, delete "(FIG. 9c,d)." and insert -- (FIGS. 9c, d). --.
Column 26, Line 33, delete "(FIG." and insert -- (FIGS. --.

In the Claims

Column 27, Line 17, Claim 1, delete "Method" and insert -- A method --.
Column 27, Line 42, Claim 2, after "according" insert -- to --.
Column 28, Line 6, Claim 7, after "method" insert -- according --.

Signed and Sealed this
Twenty-fifth Day of October, 2022

Katherine Kelly Vidal
*Director of the United States Patent and Trademark Office*